(12) United States Patent
Steurer et al.

(10) Patent No.: US 8,198,308 B2
(45) Date of Patent: Jun. 12, 2012

(54) CHEMICAL COMPOUNDS

(75) Inventors: Steffen Steurer, Vienna (AT); Peter Ettmayer, Vienna (AT); Andreas Mantoulidis, Vienna (AT); Ioannis Sapountzis, Vienna (AT); Martin Steegmaier, Reutlingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 22 days.

(21) Appl. No.: 12/946,069

(22) Filed: Nov. 15, 2010

(65) Prior Publication Data

US 2011/0059938 A1 Mar. 10, 2011

Related U.S. Application Data

(63) Continuation of application No. 11/773,508, filed on Jul. 5, 2007, now abandoned.

(30) Foreign Application Priority Data

Jul. 7, 2006 (EP) .................................... 06116826

(51) Int. Cl.
  *A61K 31/44* (2006.01)
  *C07D 401/00* (2006.01)
(52) U.S. Cl. ..................... 514/336; 548/255; 546/268.4; 514/383
(58) Field of Classification Search ................ 514/336, 514/383; 548/255; 546/268.4
See application file for complete search history.

(56) References Cited

U.S. PATENT DOCUMENTS

| | | | |
|---|---|---|---|
| 4,218,457 A | 8/1980 | Atsumi et al. | |
| 5,990,133 A | 11/1999 | Gaster et al. | |
| 6,492,403 B1 | 12/2002 | Illig et al. | |
| 7,166,628 B2 | 1/2007 | Cogan et al. | |
| 7,485,657 B2 | 2/2009 | Cogan et al. | |
| 7,511,042 B2 | 3/2009 | Cogan et al. | |
| 7,514,458 B2 | 4/2009 | Cogan et al. | |
| 7,531,560 B2 * | 5/2009 | Cogan et al. | 514/359 |
| 2006/0100204 A1 | 5/2006 | Cogan et al. | |
| 2008/0009497 A1 | 1/2008 | Wittman et al. | |
| 2008/0027070 A1 | 1/2008 | Noronha et al. | |
| 2008/0045489 A1 | 2/2008 | Chao et al. | |
| 2008/0132459 A1 | 6/2008 | Moradei et al. | |
| 2008/0182837 A1 | 7/2008 | Steurer et al. | |
| 2009/0239838 A1 | 9/2009 | Wittman et al. | |
| 2010/0240657 A1 | 9/2010 | Sapountzis et al. | |
| 2011/0124623 A1 | 5/2011 | Wittman et al. | |
| 2011/0183952 A1 | 7/2011 | Sapountzis et al. | |

FOREIGN PATENT DOCUMENTS

| | | |
|---|---|---|
| FR | 2401916 A1 | 3/1979 |
| JP | 03174153 A | 7/1991 |
| WO | 9703967 A1 | 2/1997 |
| WO | 0075120 A1 | 12/2000 |
| WO | 0162737 A2 | 8/2001 |
| WO | 03037274 A2 | 5/2003 |
| WO | 03051358 A1 | 6/2003 |
| WO | 03059886 A1 | 7/2003 |
| WO | 2004050642 A1 | 6/2004 |
| WO | 2005040152 A1 | 5/2005 |
| WO | 2005056535 A1 | 6/2005 |
| WO | 2005090333 A1 | 9/2005 |
| WO | 2005115991 A1 | 12/2005 |
| WO | 2006053227 A2 | 5/2006 |
| WO | 2007121390 A1 | 10/2007 |
| WO | 2008003770 A1 | 1/2008 |
| WO | 2009003998 A2 | 1/2009 |
| WO | 2009003999 A2 | 1/2009 |
| WO | 2011117381 A1 | 9/2011 |

OTHER PUBLICATIONS

Caplus: Chan, et al., 2002, CAS: 138:198127.
International Search Report for PCT/EP2007/056860 mailed Nov. 15, 2007.
Subasinghe, N.L. et al., "Structure-based Design, Synthesis and SAR of a Novel Series of Thiopheneamidine Urokinase Plasminogen Activator Inhibitors", Bioorganice and Medicinal Chemistry Letters, 11, 2001, pp. 1379-1382.
WO2005-030705, Part 1 of 2. pp. 1-388. Applicant: Methylgene Inc et al. Inventors: O. Moradei, et al. International Publication Date: Apr. 7, 2005. Title: Inhibitors of Histone Deacetylase.
WO2005-030705, Part 2 of 2. pp. 389-end. Applicatnt: Methylgene Inc et al. Inventors: O. Moradei, et al. International Publication Date: Apr. 7, 2005. Title: Inhibitors of Histone Deacetylase.

* cited by examiner

*Primary Examiner* — Rei-tsang Shiao
(74) *Attorney, Agent, or Firm* — Michael P. Morris; Anthony P. Bottino

(57) ABSTRACT

The present invention encompasses compounds of general formula (1)

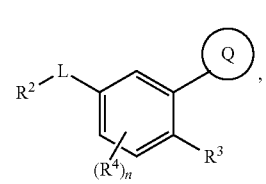

wherein the groups $R^2$ to $R^4$, L, Q and n are defined as in claim 1, which are suitable for the treatment of diseases characterized by excessive or abnormal cell proliferation, and the use thereof for preparing a medicament having the above-mentioned properties.

13 Claims, No Drawings

CHEMICAL COMPOUNDS

The present invention relates to new compounds of general formula (1)

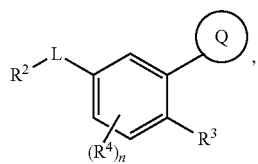

wherein the groups $R^2$ to $R^4$, L, Q and n have the meanings given in the claims and specification, the isomers and salts thereof and their use as medicaments.

BACKGROUND TO THE INVENTION

Phenyl-substituted, nitrogen-containing five-ring heteroaryls for inhibiting cytokine production and hence for treating inflammatory diseases are described in WO 2004/050642, WO 2005/056535, WO 2005/090333, WO 2005/115991 and US 2006/0100204.

The aim of the present invention is to indicate new active substances which can be used for the prevention and/or treatment of diseases characterised by excessive or abnormal cell proliferation.

DETAILED DESCRIPTION OF THE INVENTION

Surprisingly, it has been found that compounds of general formula (1), wherein the groups $R^2$ to $R^4$, L, Q and n have the meanings given hereinafter, act as inhibitors of specific signal enzymes which are involved in controlling the proliferation of cells. Thus, the compounds according to the invention may be used for example for the treatment of diseases associated with the activity of these signal enzymes and characterised by excessive or abnormal cell proliferation.

The present invention therefore relates to compounds of general formula (1)

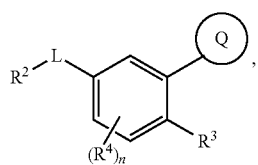

wherein

Q has a partial structure selected from among the partial structures (i)-(v)

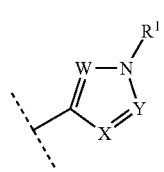

W, X and Y are each independently of one another selected from among $=CR^{5a}-$ and $=N-$, Z is in each case independently selected from among $-NR^6-$, $-O-$ and $-S-$, L is selected from among $-C(O)NH-$, $-NHC(O)-$, $-C(S)NH-$, $-NHC(S)-$, $-C(O)-$, $-C(S)-$, $-NH-$, $-S(O)-$, $-S(O)O-$, $-S(O)_2-$, $-S(O)_2O-$, $-S(O)NH-$, $-S(O)_2NH-$, $-OS(O)-$, $-OS(O)_2-$, $-OS(O)NH-$, $-OS(O)_2NH-$, $-C(O)O-$, $-C(O)S-$, $-C(NH)NH-$, $-OC(O)-$, $-OC(O)O-$, $-OC(O)NH-$, $-SC(O)-$, $-SC(O)O-$, $-SC(O)NH-$, $-NHC(NH)-$, $-NHS(O)-$, $-NHS(O)O-$, $-NHS(O)_2-$, $-NHS(O)_2O-$, $-NHS(O)_2NH-$, $-NHC(O)O-$, $-NHC(O)NH-$ and $-NHC(S)NH-$ or denotes a bond, $R^1$ is selected from among $R^a$ and $R^b$, $R^2$ denotes a 5-12 membered heteroaryl, optionally substituted by one or more, identical or different $R^{5b}$, $R^3$ and each $R^4$ is in each case independently selected from among hydrogen, halogen, $-CN$, $-NO_2$, $-NR^hR^h$, $-OR^h$, $-C(O)R^h$, $-C(O)NR^hR^h$, $-SR^h$, $-S(O)R^h$, $-S(O)_2R^h$, $C_{1-4}$alkyl, $C_{1-4}$haloalkyl, $C_{3-7}$cycloalkyl and 3-7 membered heterocycloalkyl, each $R^{5a}$ and $R^{5b}$ is selected independently of one another from among $R^a$ and $R^b$, $R^6$ is defined in the same way as $R^a$, n has the value 0, 1, 2 or 3, each $R^a$ independently of one another denotes hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is in each case independently selected from among $=O$, $-OR^c$, $C_{1-3}$haloalkyloxy, $-OCF_3$, $=S$, $-SR^c$, $=NR^c$, $=NOR^c$, $=NNR^cR^c$, =NN(R^g)C(O)NR^cR^c, —NR^cR^c, —ONR^cR^c, —N(OR^c)R^c, —N(R^g)NR^cR^c, halogen, —CF_3, —N, —NC, —OCN, —SCN, —NO, —NO_2, =N_2, —N_3, —S(O)R^c, —S(O)OR^c, —S(O)_2R^c, —S(O)_2OR^c, —S(O)NR^cR^c, —S(O)_2NR^cR^c, —OS(O)R^c, —OS(O)_2R^c, —OS(O)_2OR^c, —OS(O)NR^cR^c, —OS(O)_2NR^cR^c, —C(O)R^c, —C(O)OR^c, —C(O)SR^c, —C(O)NR^cR^c, —C(O)N(R^g)NR^cR^c, —C(O)N(R^g)OR^c, —C(NR^g)NR^cR^c, —C(NOH)R^c, —C(NOH)NR^cR^c, —OC(O)R^c, —OC(O)OR^c, —OC(O)SR^c, —OC(O)NR^cR^c, —OC(NR^g)NR^cR^c, —SC(O)R^c, —SC(O)OR^c, —SC(O)NR^cR^c, —SC(NR^g)NR^cR^c, —N(R^g)C(O)R^c, —N[C(O)R^c]_2, —N(OR^g)C(O)R^c, —N(R^g)C(NR^g)R^c, —N(R^g)N(R^g)C(O)R^c, —N[C(O)R^c]NR^cR^c, —N(R^g)C(S)R^c, —N(R^g)S(O)R^—N(Rg)S(O)OR^c, —N(R^g)S(O)_2R^c, —N[S(O)_2R^c]_2, —N(R^g)S(O)_2OR^c, —N(R^g)S(O)_2NR^cR^c, —N(R^g)[S(O)_2]_2R^c, —N(R^g)C(O)OR^c, —N(R^g)C(O)SR^c, —N(R^g)C(O)NR^cR^c, —N(R^g)C(O)NR^gNR^cR^c, —N(R^g)N(R^g)C(O)NR^cR^c, —N(R^g)C(S)NR^cR^c, —[N(R^g)C(O)]_2R^c, —N(R^g)[C(O)]_2R^c, —N{[C(O)]_2R^c}_2, —N(R^g)[C(O)]_2OR^c, —N(R^g)[C(O)]_2NR^cR^c, —N{[C(O)]_2OR^c}_2, —N{[C(O)]_2NR^cR^c}_2, 13 [N(R^g)C(O)]_2OR^c, —N(R^g)C(NR^g)OR^c, —N(R^g)C(NOH)R^c, —N(R^g)C(NR^g)SR^c and —N(R^g)C(NR^g)NR^cR^c, each $R^c$ in each case independently of one another denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^d$ denotes a suitable group and is in each case independently selected from among =O, —OR^e, $C_{1-3}$haloalkyloxy, —OCF_3, =S, —SR^e, =NR^e, =NOR^e, =NNR^eR^e, =NN(R^g)C(O)NR^eR^e, —NR^eR^e, —ONR^eR^e, —N(R^g)NR^eR^e, halogen, —CF_3, —CN, —NC, —OCN, —SCN, —NO, —NO_2, =N_2, —N_3, —S(O)R^e, —S(O)OR^e, —S(O)_2R^e, —S(O)_2OR^e, —S(O)NR^eR^e, —S(O)_2NR^eR^e, —OS(O)R^e, —OS(O)_2R^e, —OS(O)_2OR^e, —OS(O)NR^eR^e, —OS(O)_2NR^eR^e, —C(O)R^e, —C(O)OR^e, —C(O)SR^e, —C(O)NR^eR^e, —C(O)N(R^g)NR^eR^e, —C(O)N(R^g)OR^e, —C(NR^g)NR^eR^e, —C(NOH)R^e, —C(NOH)NR^eR^e, —OC(O)R^e, —OC(O)OR^e, —OC(O)SR^e, —OC(O)NR^eR^e, —OC(NR^g)NR^eR^e, —SC(O)R^e, —SC(O)OR^e, —SC(O)NR^eR^e, —SC(NR^g)NR^eR^e, —N(R^g)C(O)R^e, —N[C(O)R^e]_2, —N(OR^g)C(O)R^e, —N(R^g)C(NR^g)R^e, —N(R^g)N(R^g)C(O)R^e, —N[C(O)R^e]NR^eR^e, —N(R^g)C(S)R^e, —N(R^g)S(O)R^e, —N(R^g)S(O)OR^e, —N(R^g)S(O)_2R^e, —N[S(O)_2R^e]_2, —N(R^g)S(O)_2OR^e, —N(R^g)S(O)_2NR^eR^e, —N(R^g)[S(O)_2]_2R^e, —N(R^g)C(O)OR^e, —N(R^g)C(O)SR^e, —N(R^g)C(O)NR^eR^e, —N(R^g)C(O)NR^eNR^eR^e, —N(R^g)N(R^g)C(O)NR^eR^e, —N(R^g)C(S)NR^eR^e, —[N(R^g)C(O)]_2R^e, —N(R^g[C(O)]_2R^e, —N{[C(O)]_2R^e}_2, —N(R^g)[C(O)]_2OR^e, —N(R^g)[C(O)]_2NR^eR^e, —N{[C(O)]_2OR^e}_2, —N{[C(O)]_2NR^eR^e}_2, —[N(R^g)C(O)]_2OR^e, —N(R^g)C(NR^g)OR^e, —N(R^g)C(NOH)R^e, —N(R^g)C(NR^g)SR^e and —N(R^g)C(NR^g)NR^eR^e, each $R^e$ in each case independently of one another denotes hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^f$ denotes a suitable group and is in each case independently selected from among =O, —OR^g, $C_{1-3}$haloalkyloxy, —OCF_3, =S, —SR^g, =NR^g, =NOR^g, =NNR^gR^g, =NN(R^h)C(O)NR^gR^g, —NR^gR^g, —ONR^gR^g, —N(R^h)NR^gR^g, halogen, —CF_3, —CN, —NC, —OCN, —SCN, —NO, —NO_2, =N_2, —N_3, —S(O)R^g, —S(O)OR^g, —S(O)_2R^g, —S(O)OR^g, —S(O)NR^gR^g, —S(O)_2NR^gR^g, —OS(O)R^g, —OS(O)_2R^g, —OS(O)_2OR^g, —OS(O)NR^gR^g, —OS(O)_2NR^gR^g, —C(O)R^g, —C(O)OR^g, —C(O)SR^g, —C(O)NR^gR^g, —C(O)N(R^h)NR^gR^g, —C(O)N(R^h)OR^g, —C(NR^h)NR^gR^g, —C(NOH)R^g, —C(NOH)NR^gR^g, —OC(O)R^g, —OC(O)OR^g, —OC(O)SR^g, —OC(O)NR^gR^g, —OC(NR^h)NR^gR^g, —SC(O)R^g, —SC(O)OR^g, —SC(O)NR^gR^g, —SC(NR^h)NR^gR^g, —N(R^h)C(O)R^g, —N[C(O)R^g]_2, —N(OR^h)C(O)R^g, —N(R^h)C(NR^h)R^g, —N(R^h)N(R^h)C(O)R^g, —N[C(O)R^g]NR^gR^g, —N(R^h)C(S)R^g, —N(R^h)S(O)R^g, —N(R^h)S(O)OR^g, —N(R^h)S(O)_2R^g, —N[S(O)_2R^g]_2, —N(R^h)S(O)_2OR^g, —N(R^h)S(O)_2NR^gR^g, —N(R^h)[S(O)_2]_2R^g, —N(R^h)C(O)OR^g, —N(R^h)C(O)SR^g, —N(R^h)C(O)NR^gR^g, —N(R^h)C(O)NR^hNR^gR^g, —N(R^h)N(R^h)C(O)NR^gR^g, —N(R^h)C(S)NR^gR^g, —[N(R^h)C(O)]_2R^g, —N(R^h)[C(O)]_2R^g, —N{[C(O)]_2R^g}_2, —N(R^h)[C(O)]_2OR^g, —N(R^h)[C(O)]_2NR^gR^g, —N{[C(O)]_2OR^g}_2, —N{[C(O)]_2NR^gR^g}_2, —[N(R^h)C(O)]_2OR^g, —N(R^h)C(NR^h)OR^g, —N(R^h)C(NOH)R^g, —N(R^h)C(NR^h)SR^g and —N(R^h)C(NR^h)NR^gR^g, each $R^g$ in each case independently of one another denotes hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^h$ is in each case independently selected from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the tautomers, the racemates, the enantiomers, the diastereomers and the mixtures thereof, and optionally the pharmacologically acceptable salts thereof with the provisos that (a) if $R^2$ corresponds to pyridyl, this pyridyl is linked to L through a carbon atom adjacent to the pyridyl nitrogen and (b) the compounds 1-[5-(6-tert-butyl-3-oxo-3,4-dihydro-2H-benzo[1,4]oxazin-8-ylcarbamoyl)-2-methyl-phenyl]-1H-[1,2,3]triazole-4-carboxylic acid-(2,2-dimethyl-propyl)-amide, 1-[5-(5-tert-butyl-2-methyl-benzoxazol-7-ylcarbamoyl)-2-methyl-phenyl]-1H-[1,2,3]triazole-4-carboxylic acid-(2,2-dimethyl-propyl)-amide, 1-[5-(6-tert-butyl-3,4-dihydro-2H-benzo[1,4]oxazin-8-yl-carbamoyl)-2-methyl-phenyl]-1H-[1,2,3]triazole-4-carboxylic acid-(2,2-dimethyl-propyl)-amide, 1-[5-(5-tert-butyl-2-oxo-2,3-dihydro-benzoxazol-7-ylcarbamoyl)-2-methyl-phenyl]-1H-[1,2,3]triazole-4-carboxylic acid-(2,2-dimethyl-propyl)-amide, 1-[5-(5-tert-butyl-2,2-dimethyl-3-oxo-2,3-dihydro-benzofuran-7-ylcarbamoyl)-2-methyl-phenyl]-1H-[1,2,3]triazole-4-carboxylic acid-(2,2-dimethyl-propyl)-amide, 1-[5-(1-acetyl-6-methoxy-3,3-dimethyl-2,3-dihydro-1H-indol-5-ylcarbamoyl)-2-methyl-phenyl]-1H-[1,2,3]triazole-4-carboxylic acid-(2,2-dimethyl-propyl)-amide, 5-tert-butyl-2-methyl-2H-pyrazole-3-carboxylic acid-{3-[4-(5-methoxy-pyridin-3-yl)-[1,2,3]triazol-1-yl]-4-methyl-phenyl}-amide, 5-tert-butyl-2-p-tolyl-2H-pyrazole-3-carboxylic acid-{3-[4-(5-methoxy-pyridin-3-yl)-[1,2,3]triazol-1-yl]-4-methyl-phenyl}-amide, 5-tert-butyl-2-methyl-2H-pyrazole-3-carboxylic acid-[4-methyl-3-(4-pyridin-3-yl-[1,2,3]triazol-1-yl)-phenyl]-amide,
5-tert-butyl-2-p-tolyl-2H-pyrazole-3-carboxylic acid-[4-methyl-3-(4-pyridin-3-yl-[1,2,3]triazol-1-yl)-phenyl]-amide,
5-tert-butyl-2-methyl-2H-pyrazole-3-carboxylic acid-(3-{4-[6-(cyclopropylmethyl-amino)-pyridin-3-yl]-[1,2,3]triazol-1-yl}-4-methyl-phenyl)-amide,
5-tert-butyl-2-p-tolyl-2H-pyrazole-3-carboxylic acid-(3-{4-[6-(cyclopropylmethyl-amino)-pyridin-3-yl]-[1,2,3]triazol-1-yl}-4-methyl-phenyl)-amide,
5-tert-butyl-2-methyl-2H-pyrazole-3-carboxylic acid-{4-methyl-3-[4-(5-methyl-1-phenyl-1H-pyrazol-4-yl)-[1,2,3]triazol-1-yl]-phenyl}-amide,
5-tert-butyl-2-p-tolyl-2H-pyrazole-3-carboxylic acid-{4-methyl-3-[4-(5-methyl-1-phenyl-1H-pyrazol-4-yl)-[1,2,3]triazol-1-yl]-phenyl}-amide,
5-tert-butyl-2-methyl-2H-pyrazole-3-carboxylic acid-{3-[4-(2-cyclopropyl-3-methyl-3H-imidazol-4-yl)-[1,2,3]triazol-1-yl]-4-methyl-phenyl}-amide and
5-tert-butyl-2-p-tolyl-2H-pyrazole-3-carboxylic acid-{3-[4-(2-cyclopropyl-3-methyl-3H-imidazol-4-yl)-[1,2,3]triazol-1-yl]-4-methyl-phenyl}-amide
are excluded.

In one aspect the invention relates to compounds with the provisos that (a) if $R^1$ denotes —C(O)NR$^c$R$^c$ and L denotes (R$^2$)—NHC(O)—, then $R^2$ may be an at most 6-membered heteroaryl and (b) if $R^2$ denotes pyrazolyl and L denotes (R$^2$)—C(O)NH—, then the hydrogen at the nitrogen atom of the pyrazole ring may not be substituted by methyl or 4-methylphenyl.

In another aspect the invention relates to compounds, wherein

L is selected from among —C(O)NH—, —NHC(O)—, —S(O)NH—, —S(O)$_2$NH—, —C(NH)NH—, —NHC(NH)—, —NHS(O)— and —NHS(O)$_2$— or denotes a bond.

In another aspect the invention relates to compounds, wherein n has the value 0.

In another aspect the invention relates to compounds, wherein

Q has a partial structure selected from among the partial structures (vi)-(xiii)

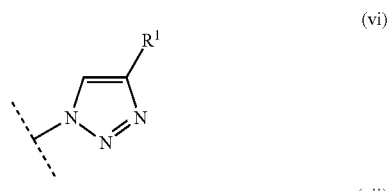

(vi)

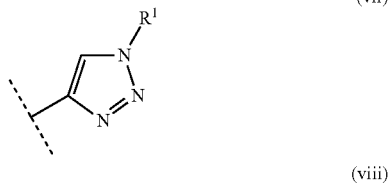

(vii)

(viii)

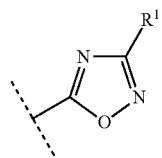

(ix)

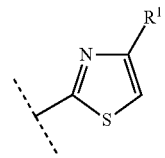

(x)

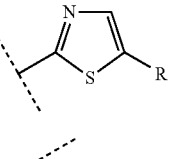

(xi)

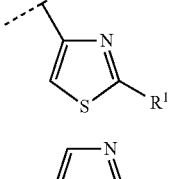

(xii)

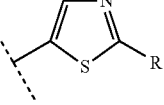

(xiii)

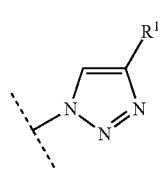

and $R^1$ is as hereinbefore defined.

In another aspect the invention relates to compounds, wherein

Q has a partial structure selected from among the partial structures (vi) and (vii)

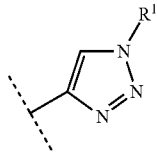

and $R^1$ is as hereinbefore defined.

In another aspect the invention relates to compounds, wherein $R^1$ denotes a group optionally substituted by one or more identical or different $R^{b1}$ and/or $R^{c1}$, selected from among $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, or $R^1$ is selected from among —C(O)OR$^{c1}$, —C(O)NR$^{c1}$R$^{c1}$ and —C(O)R$^{c1}$, each $R^{b1}$ denotes a suitable group and is in each case independently selected from among =O, —$OR^{c1}$, —$SR^{c1}$, —$NR^{c1}R^{c1}$, halogen, —CN, —$NO_2$, —$C(O)R^{c1}$, —$C(O)OR^{c1}$, —$C(O)NR^{c1}R^{c1}$, —$NHC(O)R^{c1}$, —$NHC(O)OR^{c1}$, —$NHC(O)NR^{c1}R^{c1}$, —$S(O)R^{c1}$ and —$S(O)_2R^{c1}$, each $R^{c1}$ in each case independently of one another denotes hydrogen or a group optionally substituted by one or more identical or different $R^{d1}$ and/or $R^{e1}$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^{d1}$ a suitable group and is in each case independently selected from among =O, —$OR^{e1}$, —$NR^{e1}R^{e1}$, halogen, —CN, —$NO_2$, —$C(O)R^{e1}$, —$C(O)OR^{e1}$, —$C(O)NR^{e1}R^{e1}$, —$OC(O)R^{e1}$, —$OC(O)OR^{e1}$, —$OC(O)NR^{e1}R^{e1}$, —$NHC(O)R^{e1}$, —$NHC(O)OR^{e1}$ and —$NHC(O)NR^{e1}R^{e1}$ and each $R^{e1}$ is in each case independently selected from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl.

In another aspect the invention relates to compounds, wherein $R^1$ is a group optionally substituted by one or more identical or different $R^{b1}$ and/or $R^{c1}$, selected from among $C_{6-10}$aryl, $C_{7-16}$arylalkyl, 5-12 membered heteroaryl and 6-18 membered heteroarylalkyl, and $R^{b1}$ and $R^{c1}$ are as hereinbefore defined.

In another aspect the invention relates to compounds, wherein $R^1$ is a group optionally substituted by one or more identical or different $R^{b1}$ and/or $R^{c1}$, selected from among pyridyl, pyrimidyl, thiazolyl, imidazolyl, triazolyl, pyrazolyl, pyrrolyl, furanyl, phenyl, benzyl, imidazo[1,2-b]thiazolyl, imidazo[1,2-a]pyridyl, thiazolyl-methyl and oxazolylmethyl and $R^{b1}$ and $R^{c1}$ are as hereinbefore defined.

In another aspect the invention relates to compounds, wherein $R^2$ is selected from among pyridyl, pyrazolyl, isoxazolyl, thiazolyl, imidazolyl and oxazolyl, all the above-mentioned groups optionally being substituted by one or more, identical or different $R^{5b}$ and $R^{5b}$ is as hereinbefore defined.

In another aspect the invention relates to compounds, wherein each $R^{5b}$ independently of one another is selected from among $R^{a2}$ and $R^{b2}$, each $R^{a2}$ is a group optionally substituted by one or more identical or different $R^{b2}$ and/or $R^{c2}$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^{b2}$ denotes a suitable group and is in each case independently selected from among =O, —$OR^{c2}$, —$SR^{c2}$, —$NR^{c2}R^{c2}$, halogen, —$CF_3$, —CN, —$NO_2$, —$S(O)R^{c2}$, —$S(O)_2R^{c2}$, —$S(O)NR^{c2}$, —$S(O)_2NR^{c2}R^{c2}$, —$C(O)R^{c2}$, —$C(O)OR^{c2}$, —$C(O)NR^{c2}R^{c2}$, —$OC(O)R^{c2}$, —$OC(O)OR^{c2}$, —$OC(O)NR^{c2}R^{c2}$, —$NHC(O)R^{c2}$, —$NHS(O)_2R^{c2}$, —$NHC(O)OR^{c2}$, —$NHC(O)NR^{c2}R^{c2}$, each $R^{c2}$ independently of one another denotes hydrogen or a group optionally substituted by one or more identical or different $R^{d2}$ and/or $R^{e2}$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^{d2}$ denotes a suitable group and is in each case independently selected from among =O, —$OR^{e2}$, —$NR^{e2}R^{e2}$, halogen, —CN, —$NO_2$, —$C(O)R^{e2}$, —$C(O)OR^{e2}$, —$C(O)NR^{e2}R^{e2}$, —$OC(O)R^{e2}$, —$OC(O)OR^{e2}$, —$OC(O)NR^{e2}R^{e2}$, —$NHC(O)R^{e2}$, —$NHC(O)OR^{e2}$ and —$NHC(O)NR^{e2}R^{e2}$ and each $R^{e2}$ is in each case independently selected from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl.

In another aspect the invention relates to compounds—or the pharmacologically acceptable salts thereof—of general formula (1) as pharmaceutical compositions.

In another aspect the invention relates to pharmaceutical preparations, containing as active substance one or more compounds of general formula (1) or the pharmacologically acceptable salts thereof optionally in combination with conventional excipients and/or carriers.

In another aspect the invention relates to the use of compounds of general formula (1) for preparing a pharmaceutical composition for the treatment and/or prevention of cancer, infections, inflammations and autoimmune diseases.

In another aspect the invention relates to a pharmaceutical preparation comprising a compound of general formula (1) and at least one other cytostatic or cytotoxic active substance, different from formula (1), optionally in the form of the tautomers, the racemates, the enantiomers, the diastereomers and the mixtures thereof, and optionally the pharmacologically acceptable salts thereof.

Definitions

As used herein, the following definitions apply, unless stated otherwise:

The use of the prefix $C_{x-y}$, wherein x and y each represent a natural number (x<y), indicates that the chain or ring structure or combination of chain and ring structure thus designated and mentioned in direct connection may consist of a total of not more than y and not less than x carbon atoms.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of individual sub-groups are listed below.

Straight-Chain (Unbranched) or Branched, Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tert.-butyl (1.1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl;

2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chained (Unbranched) or Branched Alkenyl:
vinyl(ethenyl); prop-1-enyl; allyl(prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:
ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

By the term heteroalkyl are meant groups which are derived from the alkyl as hereinbefore defined in its widest sense by replacing, in the hydrocarbon chains, one or more of the groups —CH$_3$ independently of one another by the groups —OH, —SH or —NH$_2$, one or more of the groups —CH$_2$— independently of one another by the groups —O—, —S— or —NH—, one or more of the groups

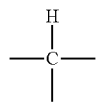

by the group

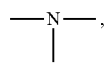

one or more of the groups =CH— by the group =N—, one or more of the groups =CH$_2$ by the group =NH or one or more of the groups ≡CH by the group ≡N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:
dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethylamino]-methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms.

The following are listed by way of example:
—CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF=CF$_2$; —CCl=CH$_2$; —CBr=CH$_2$; —CI=CH$_2$; —C≡C—CF$_3$; —CHFCH$_2$CH$_3$; —CHFCH$_2$CF$_3$ etc.

Halogen relates to fluorine, chlorine, bromine and/or iodine atoms.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system.

The following individual sub-groups are listed by way of example:

Monocyclic Hydrocarbon Rings, Saturated:
cyclopropyl; cyclobutyl; cyclopentyl; cyclohexyl; cycloheptyl etc.

Monocyclic Hydrocarbon Rings, Unsaturated:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.

Bicyclic Hydrocarbon Rings (Saturated and Unsaturated):
bicyclo[2.2.0]hexyl; bicyclo[3.2.0]heptyl; bicyclo[3.2.1]octyl; bicyclo[2.2.2]octyl; bicyclo[4.3.0]nonyl(octahydroindenyl); bicyclo[4.4.0]decyl(decahydronaphthalene); bicyclo[2.2.1]heptyl(norbornyl); (bicyclo[2.2.1]hepta-2,5-dienyl (norborna-2,5-dienyl); bicyclo[2.2.1]hept-2-enyl (norbornenyl); bicyclo[4.1.0]heptyl(norcaranyl); bicyclo-[3.1.1]heptyl(pinanyl) etc.

Spirohydrocarbon Rings (Saturated and Unsaturated):
spiro[2.5]octyl, spiro[3.3]heptyl, spiro[4.5]dec-2-ene etc.

Cycloalkylalkyl denotes the combination of the alkyl and cycloalkyl groups defined hereinbefore, in each case in their broadest sense. The alkyl group as substituent is directly linked to the molecule and is in turn substituted by a cycloalkyl group. The linking of alkyl and cycloalkyl in both groups may be effected by means of any suitable carbon atoms. The sub-groups of alkyl and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system.

Typical examples are listed below.
phenyl; naphthyl; indanyl (2,3-dihydroindenyl); 1,2,3,4-tetrahydronaphthyl; fluorenyl etc.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples are listed below:
benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono- or polysubstitution in each case, at all the hydrogen-carrying carbon and/or nitrogen atoms, independently of one another. Heteroaryl itself as substituent may be linked to the molecute via any suitable position of the ring system, both carbon and nitrogen.

Typical examples are listed below.
Monocyclic Heteroaryls:
furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls:
indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-S-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):
to tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-S-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydro-pyrimidinyl; dihydrofuryl; dihydropyranyl; tetrahydrothienyl-S-oxide; tetrahydrothienyl-S,S-dioxide; homothiomorpholinyl-S-oxide; 2,3-dihydroazet; 2H-pyrrolyl; 4H-pyranyl; 1,4-dihydropyridinyl etc.

Bicyclic Heterorings (Saturated and Unsaturated):

8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3.8-diaza-bicyclo[3.2.1]octyl; 2.5-diaza-bicyclo-[2.2.1]heptyl; 1-aza-bicyclo[2.2.2]octyl; 3.8-diaza-bicyclo[3.2.1]octyl; 3.9-diaza-bicyclo[4.2.1]nonyl; 2.6-diaza-bicyclo[3.2.2]nonyl etc.

Spiro-Heterorings (Saturated and Unsaturated):

1,4-dioxa-spiro[4.5]decyl; 1-oxa-3,8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

The term "substituted" indicates that a hydrogen atom which is bound directly to the atom in question is replaced by another atom or another group of atoms. Bivalent substituents such as for example =O, =S, =NR, =NOR, =NNRR, =NN(R)C(O)NRR, =N₂ or the like can only be substituents at carbon atoms. They require exchanging for two geminal hydrogen atoms, i.e. hydrogen atoms which are bound to the same carbon atom saturated before the substitution. Substitution by a bivalent substituent is therefore only possible at the groups —CH₃ and —CH₂—, not at the groups

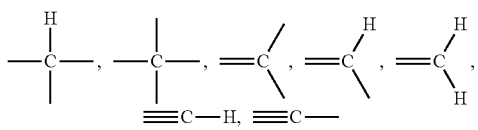

and not at aromatic carbon atoms.

Additionally, by the term "suitable substituent/suitable group" is meant a substituent which on the one hand is suitable on account of its valency and on the other hand leads to a system with chemical stability.

List of Abbreviations

| abs. | absolute, anhydrous |
| --- | --- |
| Ac | acetyl |
| Bn | benzyl |
| Boc | tert.-butyloxycarbonyl |
| Bu | butyl |
| c | concentration |
| chex | cyclohexane |
| d | day(s) |
| DBAD | di-tert.-butyl-azodicarboxylate |
| DC, TLC | thin layer chromatography |
| DCM | dichloromethane |
| DEA | diethylamine |
| DIPEA | N-ethyl-N,N-diisopropylamine (Hünig base) |
| DMAP | 4-N,N-dimethylaminopyridine |

-continued

| DME | 1,2-dimethoxyethane |
| --- | --- |
| DMF | N,N-dimethylformamide |
| DMSO | dimethylsulphoxide |
| EE | ethyl acetate |
| eq | equivalent(s) |
| ESI | electron spray ionization |
| Et | ethyl |
| EtOH | ethanol |
| h | hour |
| HATU | O-(7-azabenzotriazol-1-yl)-N,N,N',N'-tetramethyl-uronium tetrafluorophosphate |
| hex | hexyl |
| HPLC | high performance liquid chromatography |
| Hünig-base | N-ethyl-N,N-diisopropylamine |
| i | iso |
| IR | infrared spectroscopy |
| cat. | catalyst, catalytic |
| conc. | concentrated |
| b.p. | boiling point |
| LC | liquid chromatography |
| LHMDS | lithium-hexamethyldisilazane |
| soln. | solution |
| Me | methyl |
| MeOH | methanol |
| min | minutes |
| MPLC | medium pressure liquid chromatography |
| MS | mass spectrometry |
| NMP | N-methylpyrrolidone |
| NP | normal phase |
| n.a. | not available |
| Ph | phenyl |
| Pr | propyl |
| PS | polystyrene |
| Py | pyridine |
| rac | racemic |
| $R_f$(Rf) | retention factor |
| RP | reversed phase |
| RT | ambient temperature |
| TBAF | tetrabutylammonium fluoride |
| TBTU | O-(benzotriazol-1-yl)-N,N,N',N'-tetramethyl-uronium tetrafluoroborate |
| temp. | temperature |
| tert. | tertiary |
| Tf | triflate |
| TFA | trifluoroacetic acid |
| THF | tetrahydrofuran |
| TMS | trimethylsilyl |
| $t_{Ret}$ | retention time (HPLC) |
| TsOH | para-toluenesulphonic acid |
| UV | ultraviolet |

Features and advantages of the present invention will become apparent from the following detailed Examples, which illustrate the basics of the invention by way of example, without limiting its scope:

Preparation of the Compound According to the Invention

General

All the reactions are carried out—unless stated otherwise—in commercially obtainable apparatus using methods conventionally used in chemical laboratories.

Air- and/or moisture-sensitive starting materials are stored under protective gas and corresponding reactions and manipulations using them are carried out under protective gas (nitrogen or argon).

Microwave reactions are carried out in an Initiator made by Biotage or Explorer made by CEM in sealed containers (preferably 2, 5 or 20 mL), preferably with stirring.

Chromatography

For the preparative medium pressure chromatography (MPLC, normal phase) silica gel is used which is made by Millipore (named: Granula Silica Si-60A 35-70 μm) or C-18 RP-silica gel (RP-phase) made by Macherey Nagel (named: Polygoprep 100-50 C18). The thin layer chromatography is carried out on ready-made silica gel 60 TLC plates on glass (with fluorescence indicator F-254) made by Merck.

The preparative high pressure chromatography (HPLC) is carried out using columns made by Waters (named: XTerra Prep. MS C18, 5 μm, 30×100 mm or XTerra Prep. MS C18, 5 μm, 50×100 mm OBD or Symmetry C18, 5 μm, 19×100 mm or Sunfire C18 OBD, 19×100 mm, 5 μm or Sunfire Prep C 10 μm OBD 50×150 mm or X-Bridge Prep C18 5 μm OBD 19×50 mm), Agilent (named: Zorbax SB-C8 5 μm PrepHT 21.2×50 mm) and Phenomenex (named: Gemini C18 5 μm AXIA 21.2×50 mm or Gemini C18 10 μm 50×150 mm), the analytical HPLC (reaction control) with columns made by Agilent (named: Zorbax SB-C8, 5 μm, 21.2×50 mm or Zorbax SB-C8 3.5 μm 2.1×50 mm) and Phenomenex (named: Gemini C18 3 μm 2×30 mm).

HPLC-Mass Spectroscopy/UV-Spectrometry

The retention times/MS-ESI+ for characterising the examples are obtained using an HPLC-MS apparatus (high performance liquid chromatography with mass detector) made by Agilent. Compounds that elute with the injection peak are given the retention time $t_{Ret.}$=0.0 min The apparatus has the following specification:
Column: Waters, Xterra MS C18, 2.5 μm, 2.1×30 mm, Part. No. 186000592
Eluant: A: H$_2$O with 0.1% HCOOH; B: acetonitrile (HPLC grade)
Detection: MS: Positive and negative mode
Mass range: 120-900 m/z
Fragmentor: 120
Gain EMV: 1; Threshold: 150; Stepsize: 0.25; UV: 254 nm; Bandwide: 1
Injection: Inj. Vol. 5 μL
Separation: Flow 1.10 mL/min
Column temp.: 40° C.
Gradient: 0.00 min: 5% solvent B
　0.00-2.50 min: 5% 95% solvent B
　2.50-2.80 min: 95% solvent B
　2.81-3.10 min: 95% 5% solvent B In addition, the following apparatus specification is used in some cases:
Column: Waters, Xterra MS C18, 2.5 μm, 2.1×50 mm, Part. No. 186000594
Eluant: A: deion. water with 0.1% HCOOH; B: acetonitrile with 0.1% HCOOH
Detection: MS: Positive and negative mode
Mass range: 100-1200 m/z
Fragmentor: 70
Gain EMV: Threshold: 1 mAU; Stepsize: 2 nm; UV: 254 nm as well as 230 nm;
　Bandwide: 8
Injection: Standard 1 μL
Flow: 0.6 mL/min
Column temp.: 35° C.
Gradient: 0.00 min: 5% solvent B
　0.00-2.50 min: 5%→95% solvent B
　2.50-4.00 min: 95% solvent B
　4.00-4.50 min: 95%→5% solvent B
　4.50-6.00 min: 95% solvent A The compounds according to the invention may be prepared by the methods of synthesis described below, with the substituents of the general formulae having the meanings stated hereinbefore. These methods are intended to illustrate the invention without restricting it to their content or limiting the scope of the compounds claimed to these Examples. Where the preparation of the starting compounds is not described, they are commercially obtainable or may be prepared analogously to known compounds or methods described herein. Substances described in the literature are prepared according to the published methods of synthesis.

Reaction scheme A

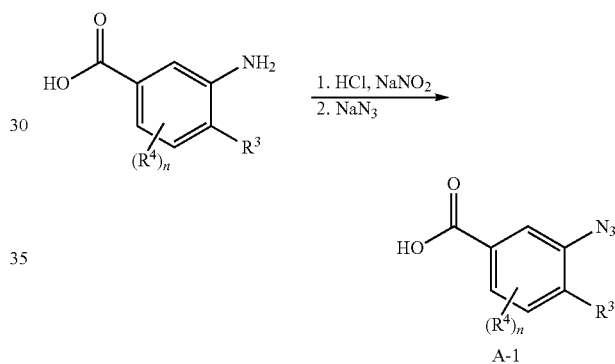

The compounds A-1 are accessed by methods known from the literature, by diazotising 3-aminobenzoic acids in hydrochloric NaNO$_2$ solution and reacting them with sodium azide to form the aromatic azides.

Reaction scheme B

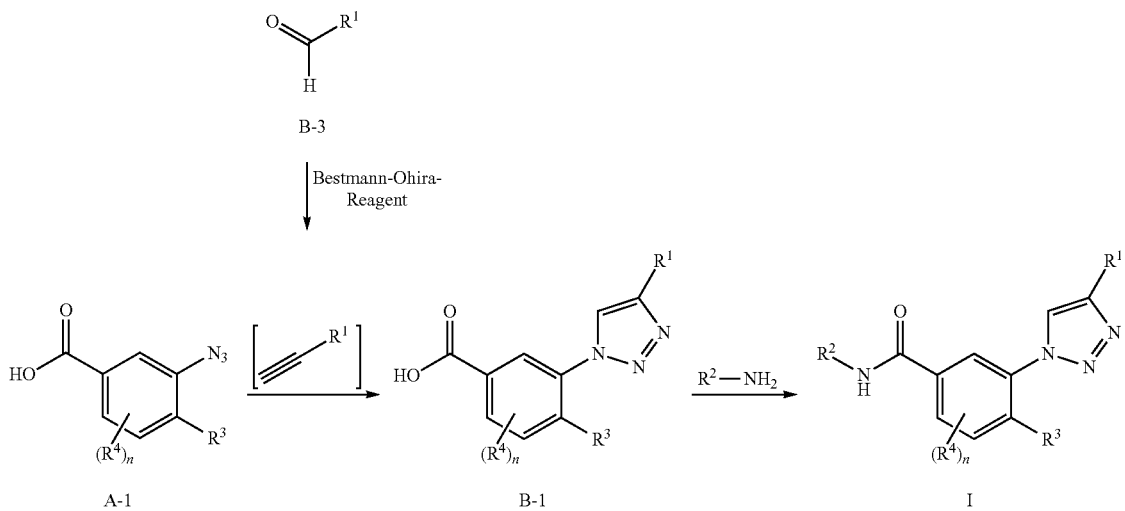

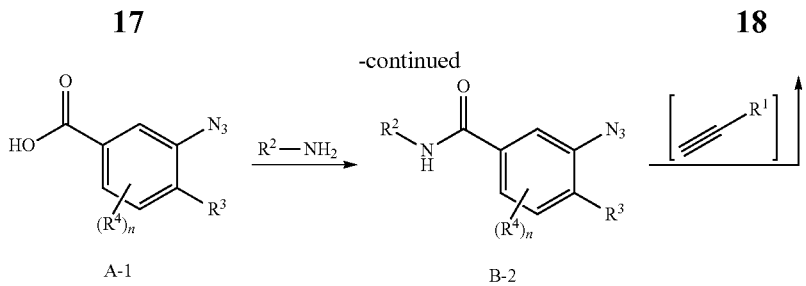

The Examples of type I are synthesised from the compounds A-1 by a cycloaddition (in order to insert the group $R^1$) and an amide coupling reaction (in order to insert the group $R^2$), and these two partial steps may be carried out in any desired order. The amide coupling is carried out using methods known from the literature with the aid of common coupling reagents, such as HATU or TBTU, or the compounds A-1 or B-1 are activated by means of thionyl chloride, oxalyl chloride or Ghosez reagent using methods known from the literature to form the corresponding acid chloride and then reacted with an amine $R^2$—$NH_2$. The amines used are commercially obtainable or are synthesised using methods known from the literature. The cycloaddition with the compounds A-1 and B-2 respectively is also carried out using methods known from the literature using a corresponding alkyne, $CuSO_4$ and sodium ascorbate.

The alkynes used to introduce the groups $R^1$ are either commercially obtainable or are prepared from commercially obtainable aldehydes or aldehydes synthesised using methods known from the literature, e.g. by means of the Bestmann-Ohira reagent.

The compounds of type I which can be prepared directly by these reaction methods are then varied still further in $R^1$ in a method known from or analogous to the literature.

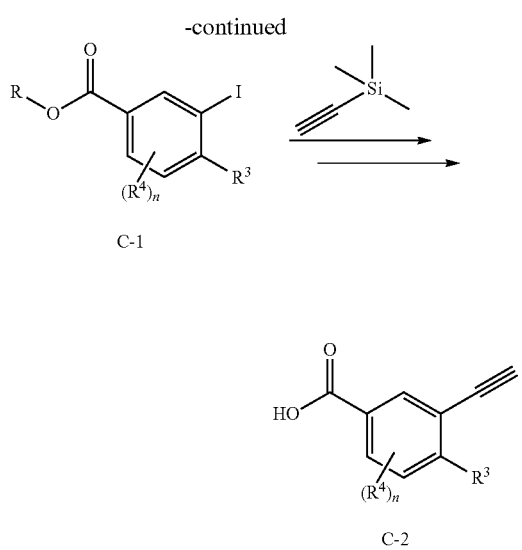

R = H or Alkyl

The compounds C-2 may be accessed in a number of ways. Using methods known from the literature compounds of type C-1 are coupled with TMS-acetylene in a Sonogashira reaction. The cleaving of the silyl group may also be carried out using methods known from the literature (e.g. with $K_2CO_3$ or TBAF). Any ester cleaving is also carried out using methods known from the literature. The compounds C-1—if they are not commercially obtainable—are in turn obtained by known methods by diazotisation and subsequent reaction with potassium iodide from the corresponding anilines.

Reaction scheme C

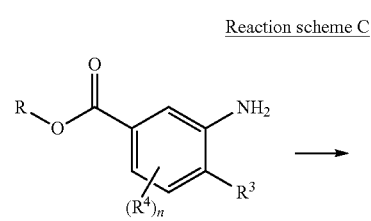

Reaction scheme D

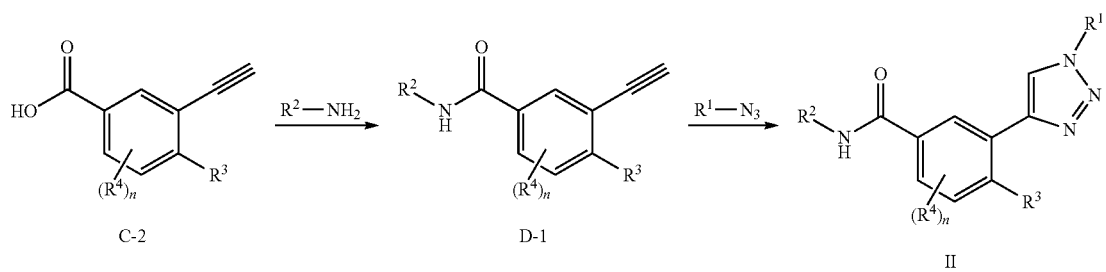

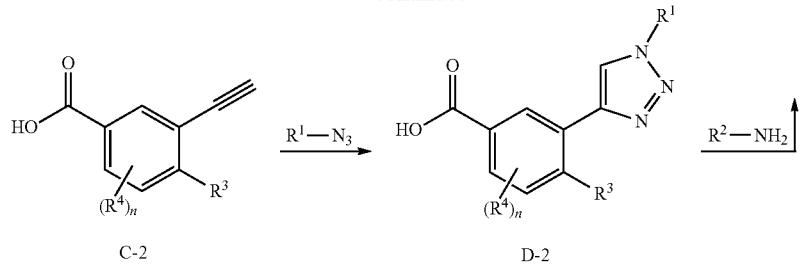

The Examples of type II are synthesised from the compounds C-2 by an amide coupling reaction (in order to introduce the group $R^2$) and a cycloaddition with an azide (in order to introduce the group $R^1$), while the two partial steps may be carried out in any order. The amide coupling is carried out using methods known from the literature with the aid of common coupling reagents, such as HATU or TBTU, or the compounds C-2 and D-2 respectively are activated by means of thionyl chloride, oxalyl chloride or Ghosez reagent using methods known from the literature to form the corresponding acid chloride and then reacted with an amine $R^2$—$NH_2$. The amines used are commercially obtainable or are synthesised using methods known from the literature. The cycloaddition with the compounds C-2 or D-1 is also carried out using methods known from the literature with the aid of $CuSO_4$ and sodium ascorbate.

Aryl or heteroaryl azides for introducing the groups $R^1$ are obtained by known methods from the corresponding amine by diazotisation and reaction with sodium azide. Arylalkyl-azides, heteroarylalkyl-azides as well as most other azides are obtained by nucleophilic substitution of the corresponding halides, for example the bromide, with sodium azide.

Reaction scheme E

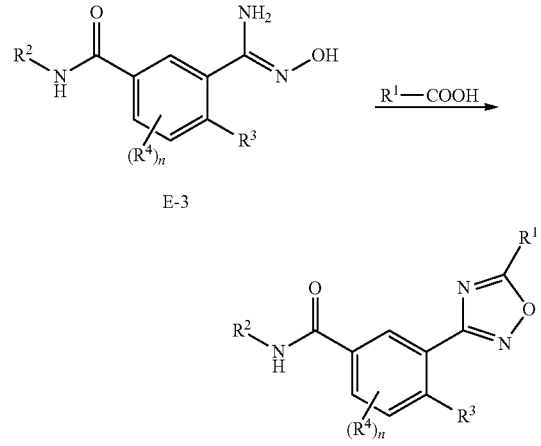

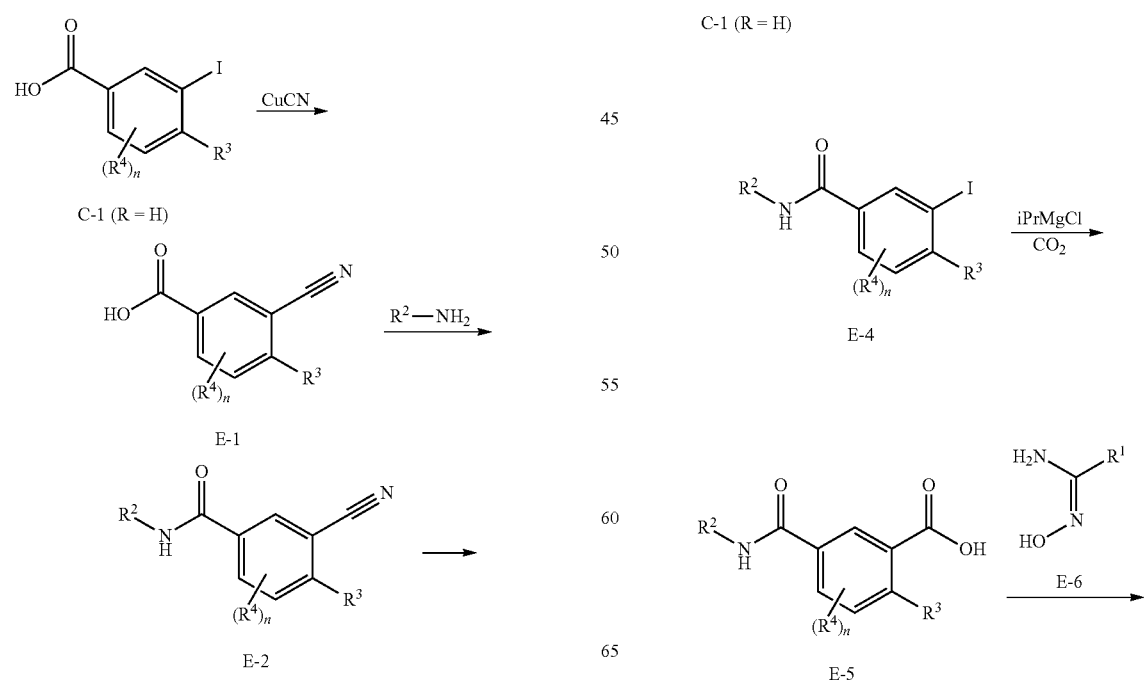

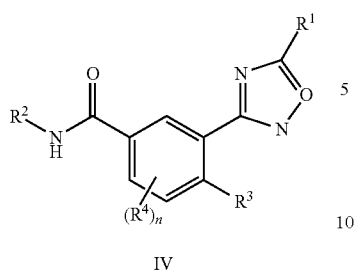

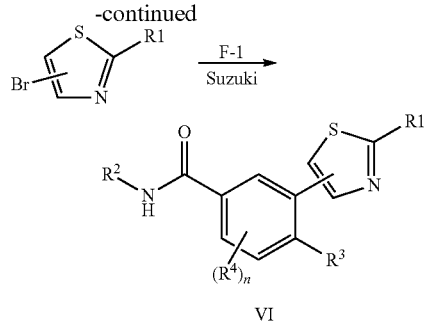

Examples of type III are synthesised via the intermediates E-2, which can be obtained starting from C-1 by reaction with CuCN with subsequent amide coupling in order to introduce the group R². Reaction of E-2 using methods known from the literature first of all with hydroxylamine to E-3 and then with activated carboxylic acids yields examples of type III.

Compounds of type IV are also obtainable starting from C-1 via the carboxylic acid intermediates E-5, which are cyclised with hydroxyamidines E-6 using methods known from the literature.

Compounds of type V and VI are synthesised via the boric acid esters F-1, which are prepared from the intermediates E-4 by methods known from the literature. Compounds of type V and VI are obtained by two successive Suzuki coupling reactions with commercially obtainable dibromothiazoles, F-1 and $R^1$—$B(OH)_2$ using methods known from the literature.

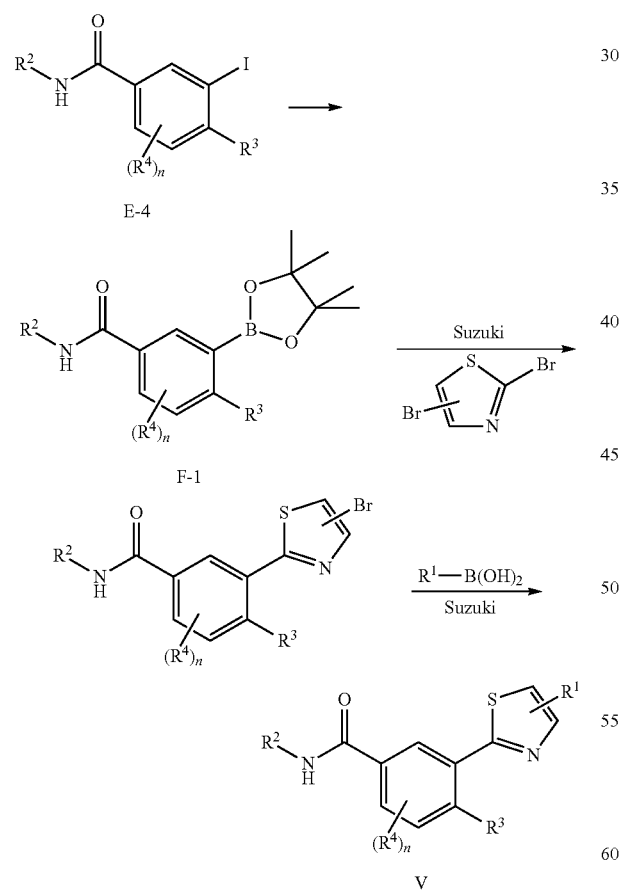

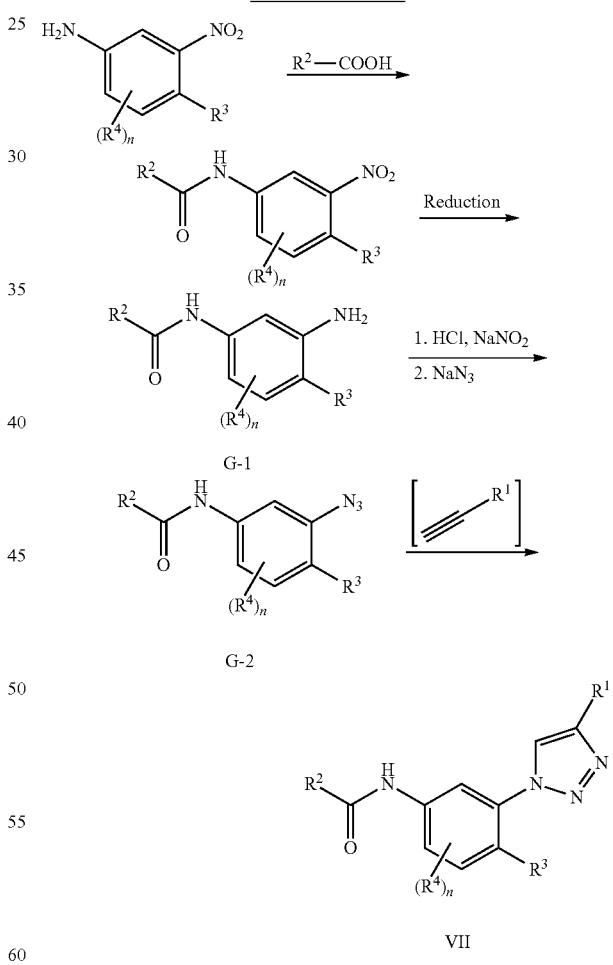

Compounds of type VII, which are prepared according to general scheme G1, have an inverted amide bond compared with those of type I (reaction scheme B). The synthesis starts from meta-nitroanilines which are obtainable commercially or using methods known from the literature. First of all, the carboxylic acid $R^2$—COOH after activation of the acid function is coupled to the aniline derivative e.g. by means of coupling reagents such as TBTU or HATU or after reaction to obtain the acid chloride, e.g. by means of oxalyl chloride, thionyl chloride or Ghosez reagent. Then the aromatic nitro group is reduced to the amine G-1 in a manner known from the literature, e.g. with iron. The amines G-1 are converted in known manner into the corresponding azides G-2, which react e.g. by means of alkynes that are commercially obtainable or that can be prepared as described in the literature in a cycloaddition to form compounds of the general type VII.

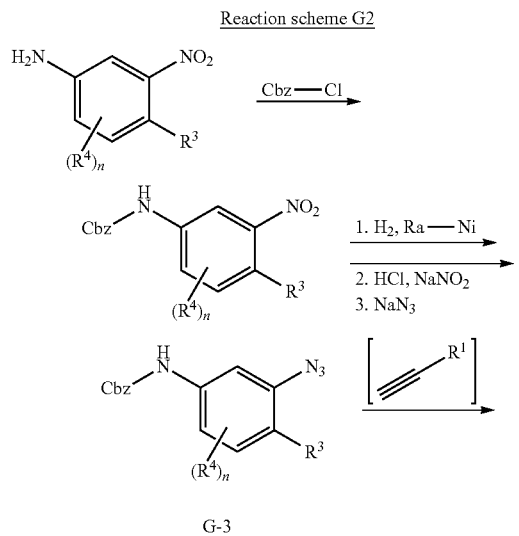

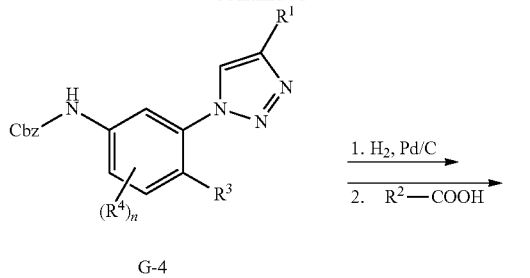

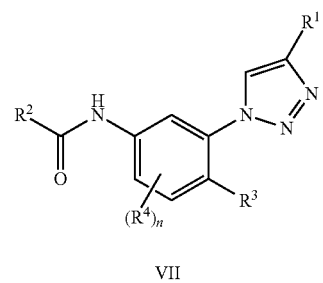

Reaction scheme G2 shows an alternative method of obtaining the compounds of type VII. Starting from the same nitroanilines, the intermediate G-3 is obtained by introducing a suitable protective group for the amino function (e.g. Cbz), subsequent reduction of the nitro group and azide formation. As a result of the subsequent cycloaddition $R^1$ is introduced and the intermediate product G-4 is obtained. The group $R^2$ may subsequently be introduced by cleaving the protective group and reacting with heteroaryl-carboxylic acids that are commercially obtainable or may be synthesised using methods known from the literature, by known amide coupling methods, such as e.g. HATU or acid chloride activation.

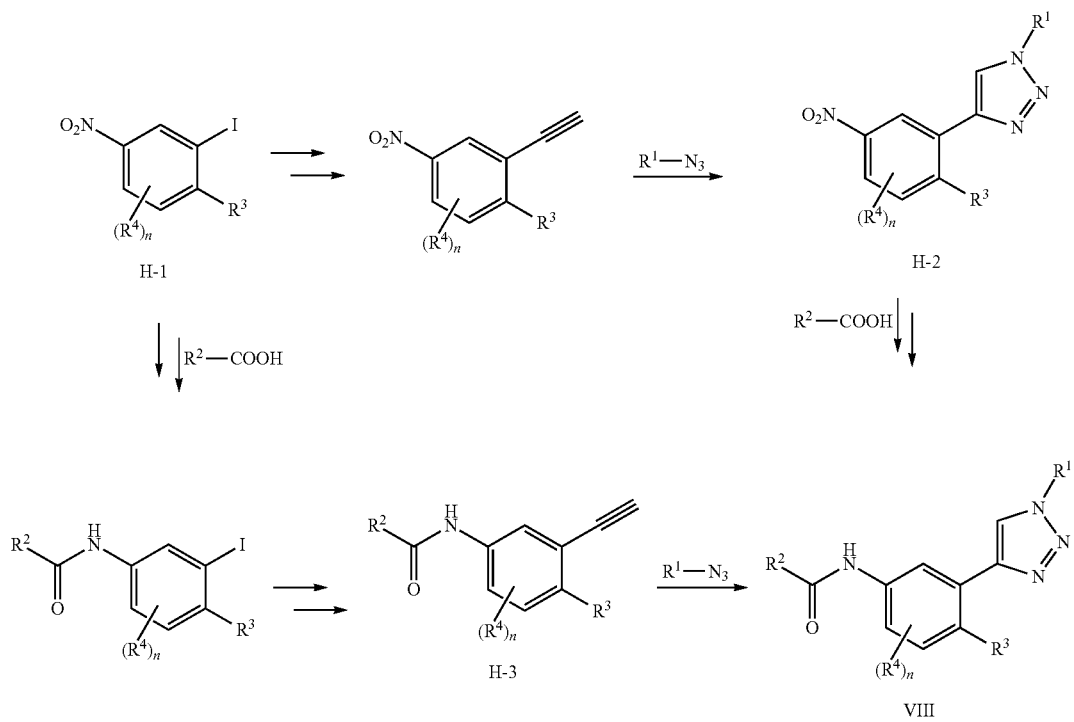

Type VIII compounds also have an inverted amide bond (analogously to type VII) and are synthesised starting from H-1 either via the intermediates H-2 or H-3 by the use of Sonogashira coupling reactions, amide couplings and cycloadditions in a suitable order, similarly to the manner described for compounds of type II in reaction scheme C and D.

The method of obtaining the inverted amide bond presented in reaction scheme G1, G2 (type VII) and H (type VIII) (based on type I and type II, respectively) can also be applied to the inverting of compounds of type III, IV, V and VI by similar transformations.

SYNTHESIS OF EXAMPLES I-1 TO I-68

Method of Synthesizing A-1a:

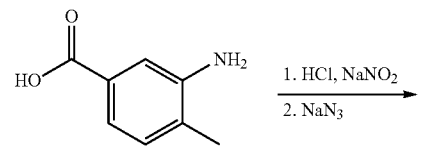

3-amino-4-methylbenzoic acid (10 g, 65.5 mmol) is dissolved in 2N HCl (300 mL), cooled to 0° C., combined with a solution of sodium nitrite (5.42 g, 69 mmol) in 30 mL water and stirred for 30 min Then a solution of sodium azide (4.73 g, 72 mmol) in 30 mL water is added dropwise, after it has all been added the mixture is stirred for a further 30 min and then heated to ambient temperature.

The precipitate of A-1a formed is filtered off, washed several times with water and then freeze-dried (HPLC-MS: $t_{Ret}$=1.61 min; MS (M+H)$^+$=178).

Other compounds A-1 are obtained analogously to this method from the corresponding 3-aminobenzoic acid derivatives.

Method of Preparing the Bestmann-Ohira Reagent:

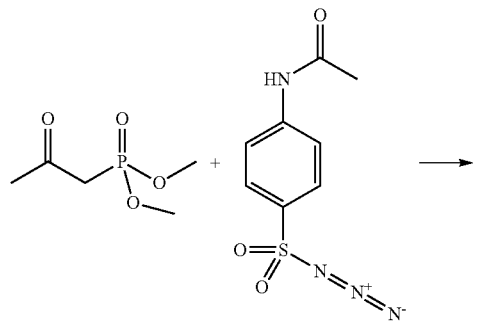

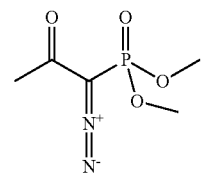

Bestmann-Ohira-Reagent (B-O)

Dimethyl-acetyl-methylphosphonate (14.123 g, 82 mmol) is placed in toluene (80 mL), cooled to 0° C. and sodium hydride (3.28 g, 60%), 82 mmol) is added batchwise thereto over a period of about 45 min After the development of gas has ended, 4-acetamidobenzenesulphonic acid azide (20.31 g, 82 mmol) dissolved in THF (30 mL) is added dropwise at 0° C. and then the mixture is stirred overnight at RT. For working up the mixture is diluted with diethyl ether (200 mL), filtered through Celite, washed repeatedly with diethyl ether and the filtrate is evaporated down under reduced pressure.

The crude Bestmann-Ohira reagent (B-O) is used in this form without further purification for the alkyne formation in the reactions that follow.

Method of Synthesising B-1a:

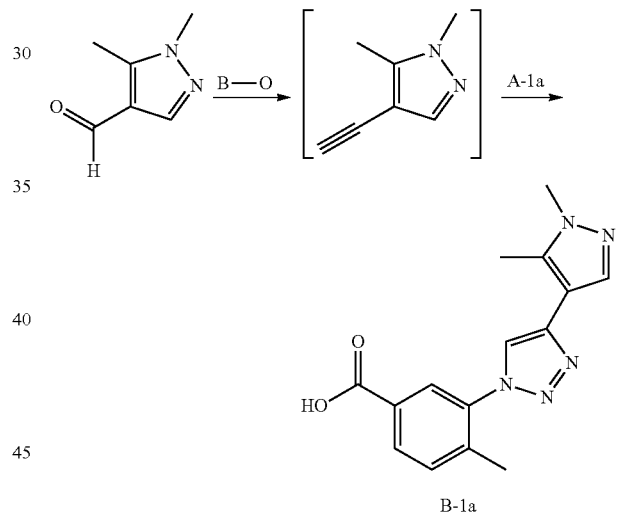

1,5-dimethyl-1H-pyrazole-4-carbaldehyde (2.803 g, 22.58 mmol) and the Bestmann-Ohira reagent (B-O, 5.964 g, 31.05 mmol) are placed in methanol (75 mL) and combined with potassium carbonate (6.241 g, 45.16 mmol). After 3 d stirring at RT the azide A-1a (2.5 g, 14.11 mmol) is added and the mixture is stirred. Then sodium ascorbate (3.075 g, 15.52 mmol) dissolved in 12.5 mL water and 28.2 mL of a 0.1M CuSO$_4$ soln. (2.82 mmol) are added and the mixture is stirred for 3 d at RT.

For working up the mixture is evaporated down under reduced pressure, mixed with water and adjusted to an acid pH (pH less than 5) by the addition of 1N hydrochloric acid solution. The precipitate formed is filtered off, washed with a little acetonitrile and dried in the vacuum dryer. B-1a may be further used directly or purified by RP-HPLC separation (HPLC-MS: $t_{Ret}$=1.59 min; MS (M+H)$^+$=298).

Other compounds B-1 are obtained analogously to this method from the corresponding A-1 intermediates.

Method of Synthesising Example I-1

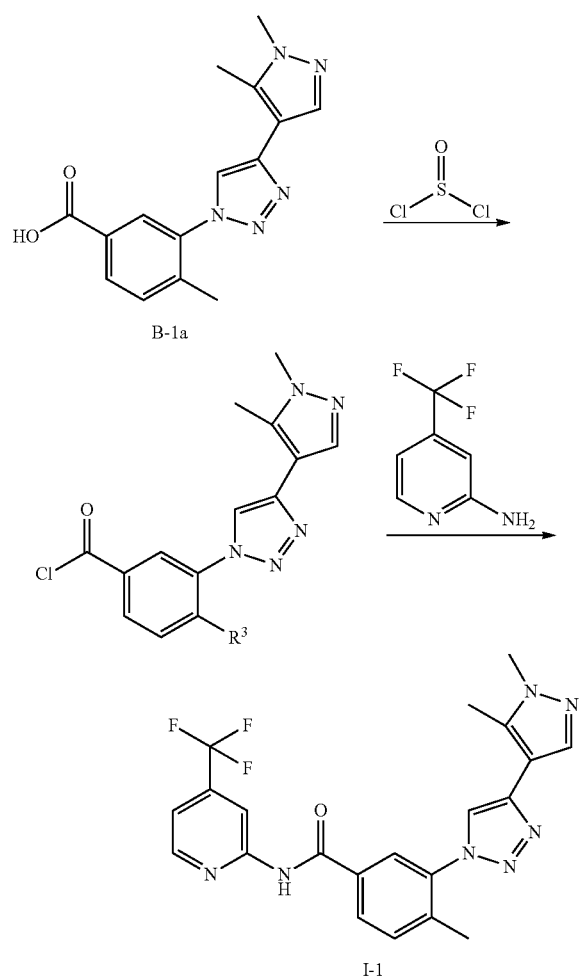

The carboxylic acid B-1a (0.9 g, 3.03 mmol) is dissolved in 1.814 mL thionyl chloride (25 mmol) and stirred for 8 h at 65° C. For working up the excess thionyl chloride is eliminated under reduced pressure, the residue is taken up in DCM (30 mL) and reacted directly with the corresponding amine.

For this, 2-amino-4-(trifluoromethyl)pyridine (0.42 g, 2.5 mmol) is placed in DCM (10 mL) and diisopropylethylamine (0.562 mL, 3.36 mmol), combined with the above freshly prepared acid chloride (in DCM) and stirred overnight at RT.

For working up the mixture is evaporated down under reduced pressure and the residue remaining is taken up in DMF. Chromatographic purification by RP-HPLC yields the compound I-1.

Analogously to the general methods described above, Examples I-2 to I-59 are synthesised from the corresponding components.

Method of Synthesising B-2a:

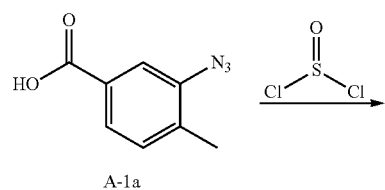

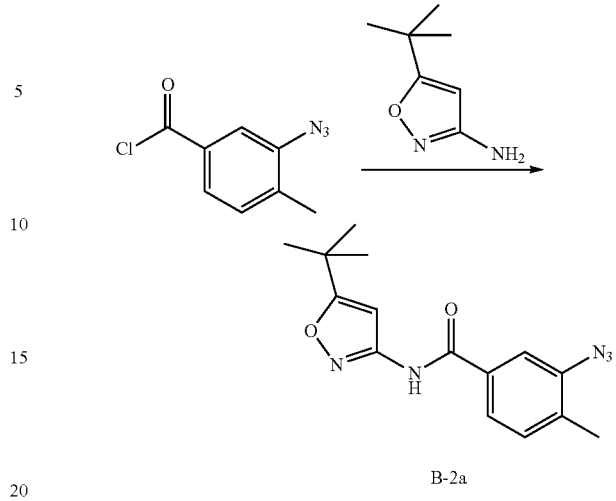

The azide A-1a (1 g, 5.655 mmol) is dissolved in 3.38 mL thionyl chloride (46.62 mmol) and stirred overnight at RT. The excess thionyl chloride is removed under reduced pressure and the solid remaining is taken up in DCM (20 mL), combined with 1.05 mL Hünig base (6.27 mmol) and then 3-amino-5-tert.-butyl-isoxazole (714.6 mg, 5.098 mmol) dissolved in DCM (10 mL) is added dropwise at RT and stirred for 30 min For working up the solvent is eliminated under reduced pressure and the residue remaining is taken up in a little DMF. By filtration and chromatographic purification by means of RP-HPLC (gradient: 15-98% acetonitrile), B-2a is obtained (HPLC-MS: $t_{Ret}$=2.36 min; MS $(M+H)^+$=300).

Other compounds B-2 are obtained analogously to this method from the corresponding A-1 intermediates.

Method of Synthesising Example I-60 and I-61 a) Method of Synthesising B-3a:

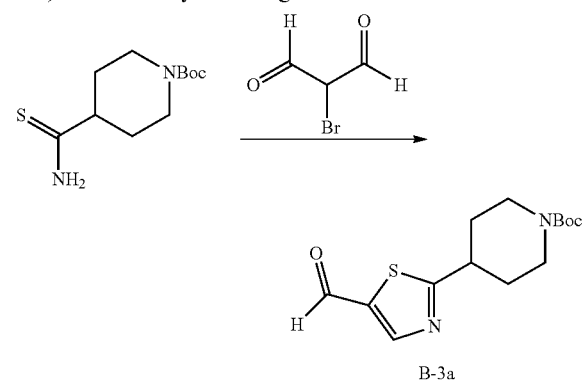

tert.-Butyl-4-(aminocarbothioyl)-tetrahydropyridine-1-(2H)-carboxylate (3.03 g, 12.4 mmol) is placed in THF (30 mL) with Hünig base (2.1 mL, 12.3 mmol) and bromine malonaldehyde (1.853 g, 12.3 mmol) is added at RT. After 3 d stirring at RT the solvent is eliminated under reduced pressure, the residue remaining is taken up in DCM and washed with aqueous sodium hydrogen carbonate solution and water. The organic phase is dried on magnesium sulphate, filtered and the filtrate is evaporated down under reduced pressure. The crude product is then purified by chromatography using silica gel (cyclohexane/EE from 60:40 to 50:50). B-3a is obtained (HPLC-MS: $t_{Ret}$=1.91 min; MS $(M+H-tBu)^+$=240).

All the other aldehydes B-3 needed to synthesise Examples I-60 to I-68 and other comparable aldehydes are obtained analogously to this method.

b) Method of synthesising the Boc-protected precursor of Examples I-60 to I-68 (V I 60 to V-I-68, taking as example V-I-60 and V-I-61, respectively):

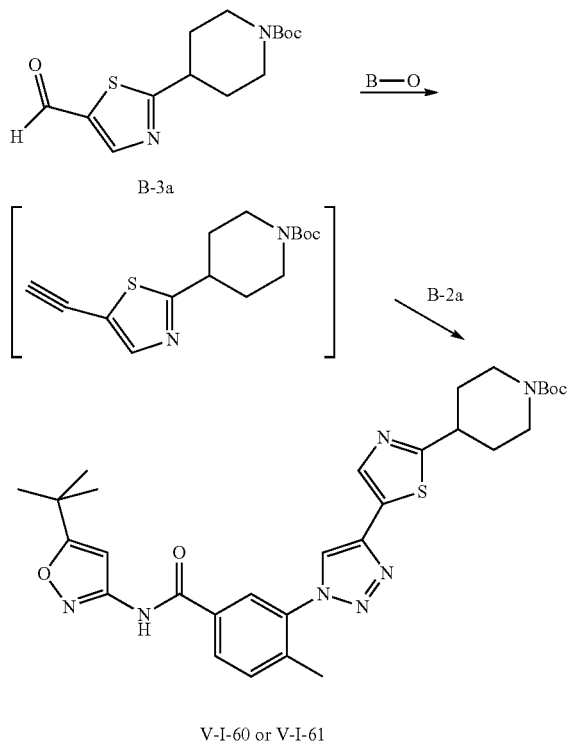

V-I-60 or V-I-61

Aldehyde B-3a (437.6 mg, 1.476 mmol) and the Bestmann-Ohira reagent (B-O, 415.3 mg, 2.162 mmol) are dissolved in MeOH (15 mL), combined with potassium carbonate (323 mg, 2.337 mmol) and stirred overnight at RT. Then the azide B-2a (217 mg, 0.725 mmol) is added, followed by sodium ascorbate (158.5 mg, 0.8 mmol) dissolved in water (1 mL) and 1.5 mL of a 0.1N $CuSO_4$ solution (0.15 mmol). After 5 d at RT the mixture is evaporated down under reduced pressure, combined with semiconcentrated $NaHCO_3$ solution and extracted several times with EE. The combined organic phases are dried on magnesium sulphate, filtered, evaporated down under reduced pressure and the crude product is further used directly in this form. V-I-60 and V-I-61 are obtained (HPLC-MS: $t_{Ret}$=2.18 min; MS $(M+H)^+$=292).

Analogously to this method, all the other aldehydes B-3, needed for synthesising Examples I-60 to I-68, or other additional aldehydes comparable therewith, are reacted with the corresponding components B-2 and the compounds V-I-62 to V-I-68 or corresponding other compounds are obtained.

c) General method of synthesising Examples I-60 to I-68 by cleaving the Boc-protective group and optionally additionally carrying out reductive amination (based on the example of the synthesis of I-60 or I-61):

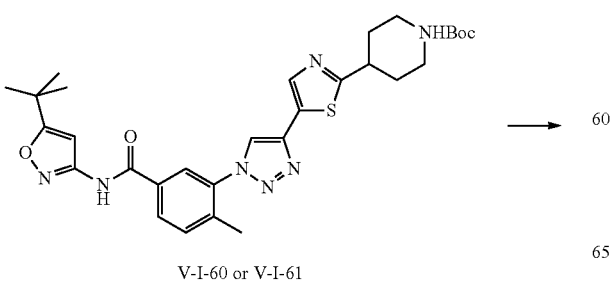

V-I-60 or V-I-61

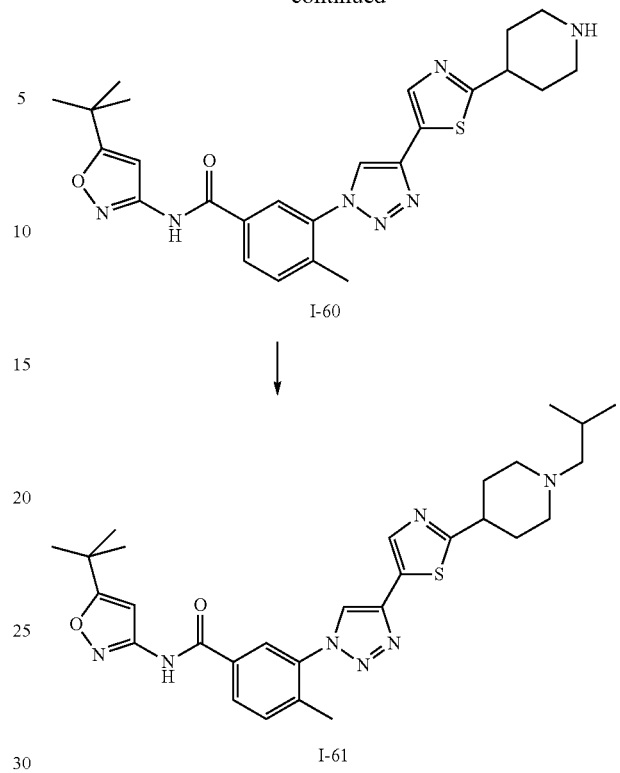

V-I-60 or V-I-61 (429 mg, 0.725 mmol) is dissolved in DCM (50 mL) and at RT combined with trifluoroacetic acid (3.8 mL). After 45 min stirring at RT water is added, the mixture is made slightly basic by the addition of NaOH solution and the organic phase is separated off. The aqueous phase is extracted twice more with DCM, the combined organic phases are dried on magnesium sulphate and filtered and the filtrate is evaporated down under reduced pressure. The residue remaining is taken up in acetonitrile and water, frozen and finally freeze-dried.

The compound I-60 thus obtained (75.3 mg, 0.153 mmol) is dissolved in DMF (1 mL), combined with isobutyraldehyde at RT (16 µL, 0.176 mmol) and stirred for 15 min. Acetic acid (9.636 µL, 0.168 mmol) and sodium triacetoxyborohydride (32.8 mg, 0.155 mmol) are added to this reaction solution and the mixture is stirred for 3 d at RT.

For working up the mixture is evaporated down under reduced pressure, the residue is taken up in a little DMF, chromatographed through a preparative RP-HPLC-MS apparatus (gradient: 10-98% acetonitrile) and the purified compound I-61 is obtained.

Analogously to the general methods a)-c) described above, Examples I-62 to I-68 or comparable additional examples may be obtained from the corresponding precursors, which are either commercially obtainable or may be prepared using methods known from the literature.

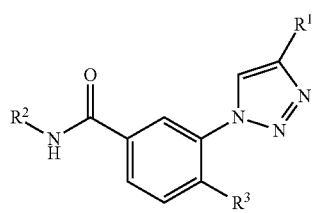

Examples I-1 to I-68

| Example | R¹ | R² | R³ | $t_{Ret}$(HPLC) [min] | MS (M + H)⁺ |
|---|---|---|---|---|---|
| I-1 | 1,5-dimethylpyrazol-4-yl | 4-(trifluoromethyl)pyridin-2-yl | CH₃ | 2.08 | 442 |
| I-2 | 1,5-dimethylpyrazol-4-yl | 1,3-dimethylpyrazol-5-yl | CH₃ | 1.45 | 391 |
| I-3 | 1,5-dimethylpyrazol-4-yl | 5-tert-butylisoxazol-3-yl | CH₃ | 1.94 | 420 |
| I-4 | 1,5-dimethylpyrazol-4-yl | 3,5-dichloropyridin-2-yl | CH₃ | 1.71 | 442 |
| I-5 | 1,5-dimethylpyrazol-4-yl | 4-tert-butylthiazol-2-yl | CH₃ | 2.07 | 436 |
| I-6 | 1,5-dimethylpyrazol-4-yl | 3-tert-butyl-1H-pyrazol-5-yl | CH₃ | 1.72 | 419 |
| I-7 | 1,5-dimethylpyrazol-4-yl | 3-tert-butyl-1-methylpyrazol-5-yl | CH₃ | 1.91 | 433 |

-continued

| Example | R¹ | R² | R³ | $t_{Ret}$ (HPLC) [min] | MS (M + H)⁺ |
|---|---|---|---|---|---|
| I-8 | 1,5-dimethylpyrazol-4-yl | 3-tert-butyl-1-(2,2,2-trifluoroethyl)pyrazol-5-yl | CH₃ | 2.11 | 501 |
| I-9 | 1,5-dimethylpyrazol-4-yl | 3-tert-butyl-1-(ethoxycarbonylmethyl)pyrazol-5-yl | CH₃ | 2.02 | 505 |
| I-10 | 1,5-dimethylpyrazol-4-yl | 3-tert-butyl-1-cyclopentylpyrazol-5-yl | CH₃ | 2.31 | 487 |
| I-11 | 1,5-dimethylpyrazol-4-yl | 3-tert-butyl-1-phenylpyrazol-5-yl | CH₃ | 2.16 | 495 |
| I-12 | 1,5-dimethylpyrazol-4-yl | 3-tert-butyl-1-(4-methoxyphenyl)pyrazol-5-yl | CH₃ | 2.15 | 525 |

-continued

| Example | R¹ | R² | R³ | $t_{Ret}$ (HPLC) [min] | MS (M + H)⁺ |
|---|---|---|---|---|---|
| I-13 | 1,5-dimethylpyrazol-4-yl | 3-tert-butyl-1-(4-chlorophenyl)-pyrazol-5-yl | CH₃ | 2.28 | 520 |
| I-14 | 1,5-dimethylpyrazol-4-yl | 3-tert-butyl-1-(2,4-dichlorophenyl)-pyrazol-5-yl | CH₃ | 2.3 | 563 |
| I-15 | 1,5-dimethylpyrazol-4-yl | 3,5-dimethylisoxazol-4-yl | CH₃ | 1.68 | 392 |
| I-16 | 1,5-dimethylpyrazol-4-yl | 1-methylpyrazol-3-yl | CH₃ | 1.63 | 377 |
| I-17 | 1,5-dimethylpyrazol-4-yl | 5-methylisoxazol-3-yl | CH₃ | 1.75 | 378 |
| I-18 | 1,5-dimethylpyrazol-4-yl | thiazol-2-yl | CH₃ | 1.77 | 380 |

| Example | R¹ | R² | R³ | t_Ret (HPLC) [min] | MS (M + H)⁺ |
|---|---|---|---|---|---|
| I-19 | 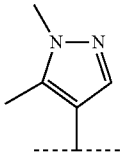 | 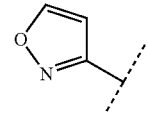 | CH₃ | 1.69 | 364 |
| I-20 | 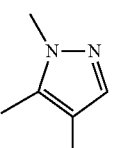 | 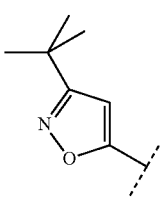 | CH₃ | | |
| I-21 | 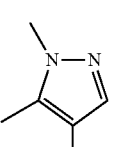 | 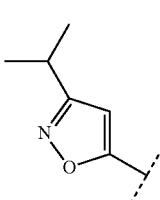 | CH₃ | | |
| I-22 | 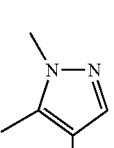 | 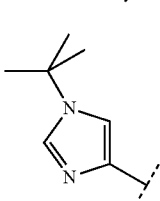 | CH₃ | | |
| I-23 | 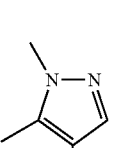 | 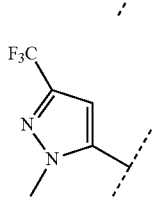 | CH₃ | | |
| I-24 | 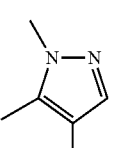 | 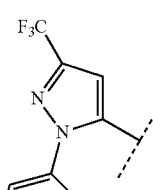 | CH₃ | | |
| I-25 | 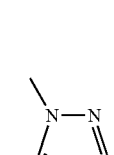 | 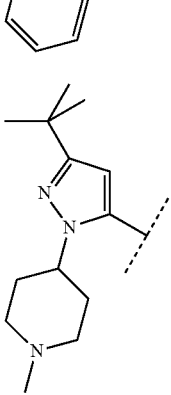 | CH₃ | | |

-continued

| Example | R¹ | R² | R³ | t$_{Ret}$(HPLC) [min] | MS (M + H)⁺ |
|---|---|---|---|---|---|
| I-26 | 1,5-dimethyl-1H-pyrazol-4-yl | 5-tert-butyl-isoxazol-3-yl | Cl | | |
| I-27 | 1,5-dimethyl-1H-pyrazol-4-yl | 3-tert-butyl-1H-pyrazol-5-yl | Cl | | |
| I-28 | 1-methyl-5-phenyl-1H-pyrazol-4-yl | 3-tert-butyl-1-methyl-1H-pyrazol-5-yl | CH₃ | 2.14 | 495 |
| I-29 | 1-methyl-5-phenyl-1H-pyrazol-4-yl | 5-tert-butyl-isoxazol-3-yl | CH₃ | 2.30 | 482 |
| I-30 | pyridin-3-yl | 1-ethyl-1H-pyrazol-5-yl | CH₃ | 1.33 | 374 |
| I-31 | pyridazin-4-yl | 4-(trifluoromethyl)pyridazin-2-yl | CH₃ | 1.76 | 425 |
| I-32 | pyridazin-4-yl | 4-tert-butyl-thiazol-2-yl | CH₃ | 2.07 | 419 |

-continued
| Example | R¹ | R² | R³ | t$_{Ret}$(HPLC) [min] | MS (M + H)⁺ |
|---|---|---|---|---|---|
| I-33 | 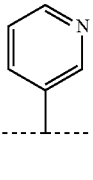 | 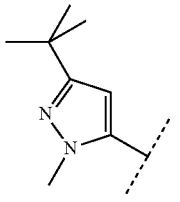 | CH₃ | 1.73 | 416 |
| I-34 | 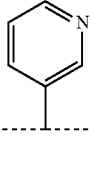 | 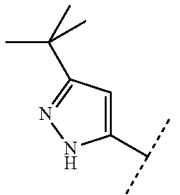 | CH₃ | 1.72 | 402 |
| I-35 | 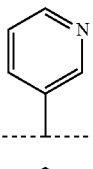 | 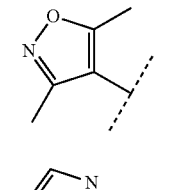 | CH₃ | 1.40 | 375 |
| I-36 | 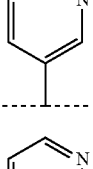 | 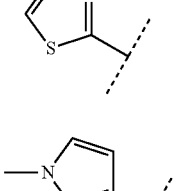 | CH₃ | 1.51 | 363 |
| I-37 | 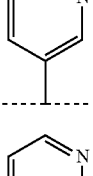 | 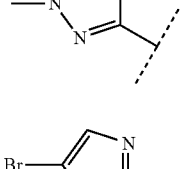 | CH₃ | 1.25 | 360 |
| I-38 | 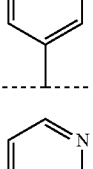 | 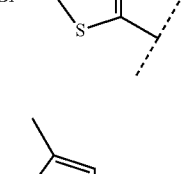 | CH₃ | 1.87 | 441/443 |
| I-39 | 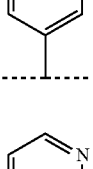 | 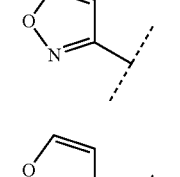 | CH₃ | 1.52 | 361 |
| I-40 | 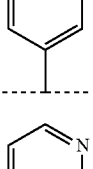 | 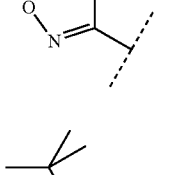 | CH₃ | 1.36 | 347 |
| I-41 | 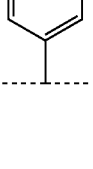 | 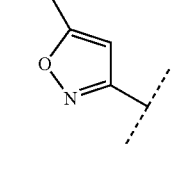 | CH₃ | 1.90 | 403 |

-continued

| Example | R¹ | R² | R³ | t_Ret (HPLC) [min] | MS (M + H)⁺ |
|---|---|---|---|---|---|
| I-42 | 4-pyridyl | 3-tert-butyl-1H-pyrazol-5-yl | CH₃ | 1.56 | 402 |
| I-43 | pyrimidin-5-yl | 3-tert-butyl-1H-pyrazol-5-yl | CH₃ | 1.80 | 403 |
| I-44 | pyrimidin-5-yl | 5-tert-butylisoxazol-3-yl | CH₃ | 2.02 | 404 |
| I-45 | 5-methoxypyridin-3-yl | 3-tert-butyl-1H-pyrazol-5-yl | CH₃ | 1.87 | 432 |
| I-46 | thiazol-5-yl | 4-(trifluoromethyl)pyridin-2-yl | CH₃ | 2.09 | 431 |
| I-47 | thiazol-5-yl | 4-(trifluoromethyl)-1,3-thiazol-2-yl | CH₃ | 2.09 | 437 |
| I-48 | thiazol-5-yl | 4-tert-butyl-1,3-thiazol-2-yl | CH₃ | 2.25 | 425 |

-continued
| Example | R¹ | R² | R³ | t_Ret (HPLC) [min] | MS (M + H)⁺ |
|---|---|---|---|---|---|
| I-49 | 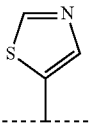 | 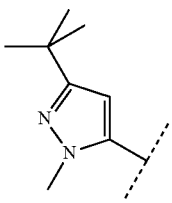 | CH₃ | 1.94 | 422 |
| I-50 |  | 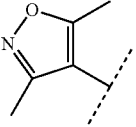 | CH₃ | 1.67 | 381 |
| I-51 | 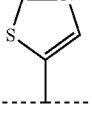 | 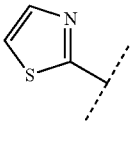 | CH₃ | 1.80 | 369 |
| I-52 | 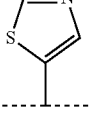 | 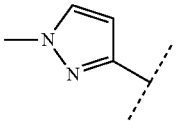 | CH₃ | 1.64 | 366 |
| I-53 | 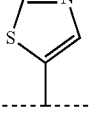 | 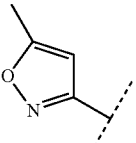 | CH₃ | 1.79 | 367 |
| I-54 | 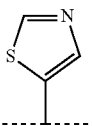 | 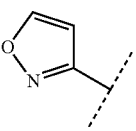 | CH₃ | 1.67 | 353 |
| I-55 | 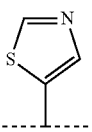 | 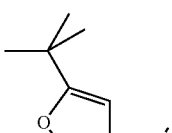 | CH₃ | 2.10 | 409 |
| I-56 |  | 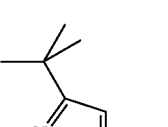 | CH₃ | 1.90 | 408 |

-continued

| Example | R¹ | R² | R³ | t_Ret (HPLC) [min] | MS (M + H)⁺ |
|---|---|---|---|---|---|
| I-57 | methyl ester group | tert-butyl isoxazole | CH₃ | | |
| I-58 | neopentyl amide | tert-butyl isoxazole | CH₃ | | |
| I-59 | 2-pyridyl amide | tert-butyl isoxazole | CH₃ | | |
| I-60 | piperidinyl thiazole | tert-butyl isoxazole | CH₃ | 1.62 | 492 |
| I-61 | 1-isobutyl-piperidinyl thiazole | tert-butyl isoxazole | CH₃ | 1.72 | 548 |
| I-62 | 1-(cyclopropylmethyl)-piperidinyl thiazole | tert-butyl isoxazole | CH₃ | 1.71 | 546 |

| Example | R¹ | R² | R³ | t_Ret (HPLC) [min] | MS (M + H)⁺ |
|---|---|---|---|---|---|
| I-63 | 4-(piperidin-4-yl)thiazol-5-yl | 3-tert-butyl-1H-pyrazol-5-yl | CH₃ | 1.51 | 491 |
| I-64 | 2-(1-methylpiperidin-4-yl)thiazol-5-yl | 5-tert-butylisoxazol-3-yl | CH₃ | | |
| I-65 | 2-(1-cyclobutylpiperidin-4-yl)thiazol-5-yl | 5-tert-butylisoxazol-3-yl | CH₃ | | |
| I-66 | 2-(1-methylazetidin-3-yl)thiazol-5-yl | 5-tert-butylisoxazol-3-yl | CH₃ | | |
| I-67 | 2-(1-methylpiperidin-4-yl)thiazol-5-yl | 3-tert-butyl-1H-pyrazol-5-yl | CH₃ | | |

| Example | R¹ | R² | R³ | t_Ret (HPLC) [min] | MS (M + H)⁺ |
|---|---|---|---|---|---|
| I-68 | 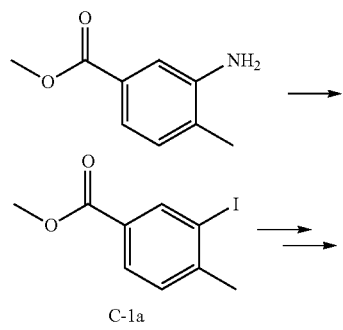 | 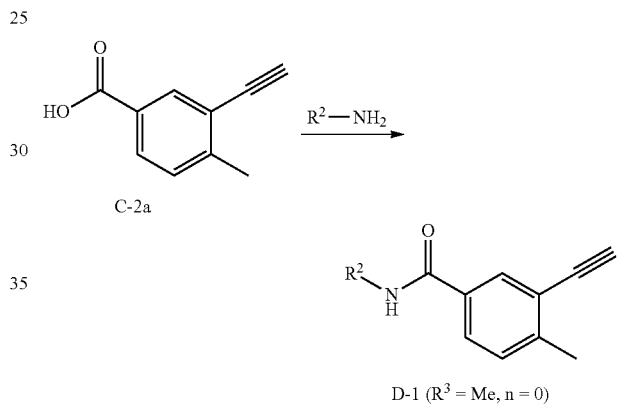 | $CH_3$ | | |

Synthesis of Examples II-1 to II-10

Method of synthesising C-2a:

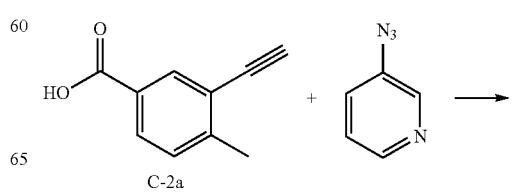

Methyl 3-amino-4-methylbenzoate (1.652 g, 10 mmol) is dissolved in 35% sulphuric acid (18 mL) and acetic acid (6 mL) and cooled to 0° C. Then a solution of sodium nitrite (0.76 g, 11 mmol) in 3 mL water is added dropwise, the mixture is stirred for 1 h at 0° C. and for 1 h at RT, then a solution of potassium iodide (2.0 g, 12 mmol) in 4 mL water is added and the mixture is stirred for 2 h. For working up the reaction mixture is combined with DCM, extracted twice, the combined organic phases are dried on sodium sulphate, filtered and evaporated down under reduced pressure. Chromatographic purification of the residue obtained through silica gel (5% EE in cyclohexane) yields C-1a (HPLC-MS: $t_{Ret}$=3.89 min; MS (M+H)⁺=277).

C-1a (0.2 g, 0.724 mmol) is placed with bis-triphenylphosphine-palladium dichloride (25.424 mg, 0.036 mmol) and copper(I)iodide under protective gas in abs. THF (3 mL) and triethylamine (1 mL). Then trimethylsilyl-ethyne is added at RT and the mixture is stirred overnight. For working up it is diluted with EE, poured onto 0.5M ammonia solution and the aqueous phase is again extracted with EE. The combined organic phases are washed with 0.5M hydrochloric acid and saturated sodium chloride solution, again extracted with EE, dried on sodium sulphate, filtered and evaporated down under reduced pressure.

The residue is combined with methanolic KOH (1 mL) and stirred for 2 h at RT. The reaction mixture is diluted with EE, poured onto 5% NaHCO₃ solution and extracted twice with EE. The combined organic phases are washed with saturated sodium chloride solution, dried on sodium sulphate, filtered and evaporated down under reduced pressure. Chromatographic purification through a short silica gel frit yields C-2a (HPLC-MS: $t_{Ret}$=3.65 min; MS (M+H)⁺=175).

Other compounds C-2 are obtained analogously to this method from the corresponding 3-aminobenzoic acid derivatives.

General Method of Synthesising the Intermediates D-1:

The carboxylic acid C-2a (1.00 mmol) is dissolved in abs. THF (2.5 mL) and abs. DCM (10 mL) and at RT α-chloroenamine reagent (Ghosez reagent, 1.10 mmol) is added dropwise. After 1 h at RT the amine (0.95 mmol) is added, DIPEA (2.50 mmol) is added dropwise and the mixture is stirred for 24 h.

For working up the mixture is diluted with EE, made acidic with 1M hydrochloric acid solution, the aqueous phase is repeatedly extracted with EE, the combined organic phases are dried on magnesium sulphate, filtered and evaporated down under reduced pressure. The residue remaining is purified by RP-HPLC separation and the corresponding compound D-1 is obtained.

Analogously to this method compounds D-1 are generally obtained from the corresponding C-2 intermediates.

Method of Synthesising the Intermediates D-2a:

-continued

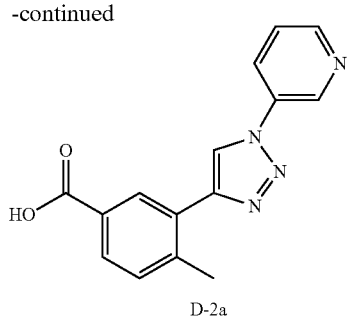

D-2a 15 mL 1M sodium ascorbate solution and 20 mL 0.1M CuSO$_4$ solution are successively added to the carboxylic acid C-2a (2.00 g, 12.5 mmol) and the azide (1.12 g, 9.32 mmol) dissolved in MeOH (200 mL). The mixture is stirred for 8 d at RT. The precipitate of C-2a formed is filtered off, washed with a little water and dried in vacuo (HPLC-MS: $t_{Ret}$=1.64 min; MS (M+H)$^+$=281).

Other compounds D-2 are obtained analogously to this method from the corresponding C-2 intermediates.

General Method of Synthesising Compounds of Type II (Variant 1):

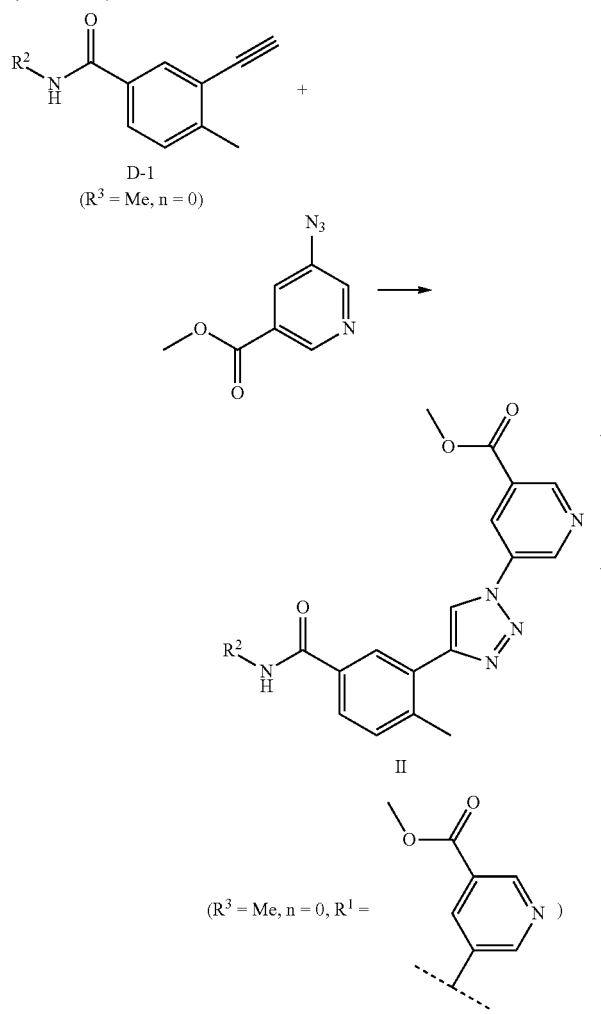

The alkyne D-1 (1.00 mmol) and the azide (1.10 mmol) are dissolved in 10 mL acetonitrile/MeOH (1:1), combined with 1.2 mL triethylamine and 2.2 mL 1M sodium ascorbate solution and after 1 minute 2.1 mL of 0.1M CuSO$_4$ solution are added. The reaction mixture is stirred overnight at RT, then once the reaction is complete the mixture is diluted with some DMF and filtered. Chromatographic purification by RP-HPLC yields compounds of type II.

Additional compounds of type II are obtained from the corresponding intermediates D-1 and the corresponding azides analogously to this method.

General Method of Synthesising compounds of Type II (Variant 2):

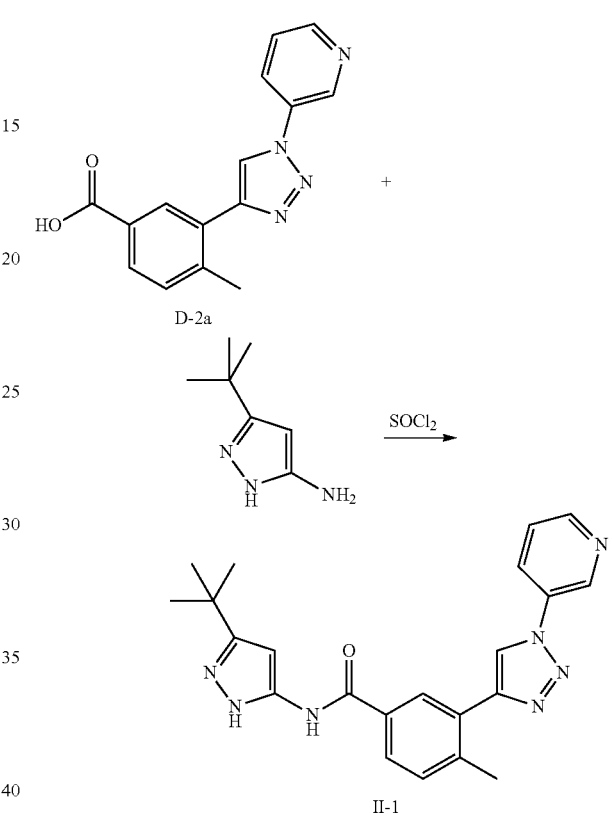

The carboxylic acid D-2a (152 mg, 0.54 mmol) is dissolved in thionyl chloride (2.0 mL) and heated for 6 h at 65° C. Then the mixture is evaporated down using the rotary evaporator, the residue is taken up in DCM (10 mL) and cooled to 0° C. A solution of the amine (68.0 mg, 0.49 mmol) and Hünig-base (98 µL, 0.60 mmol) in DCM (5 mL) are slowly added dropwise, then the cooling is removed and the mixture is stirred for 20 h. The reaction mixture is evaporated down using the rotary evaporator, taken up in DMF and the purified compound II-1 is obtained by RP-HPLC.

Analogously to this method other compounds of type II are obtained from the corresponding intermediates D-2 and the corresponding amines (cf. the Table that follows).

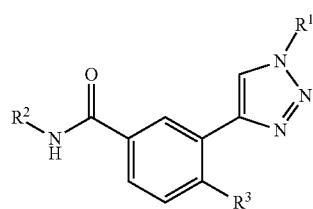

Examples II-1 to II-10

| Example | R¹ | R² | R³ | $t_{Ret}$(HPLC) [min] | MS (M + H)⁺ |
|---|---|---|---|---|---|
| II-1 | 3-pyridyl | 3-tert-butyl-1H-pyrazol-5-yl | CH₃ | 1.91 | 402 |
| II-2 | 3-pyridyl | 5-tert-butyl-isoxazol-3-yl | CH₃ | 2.14 | 403 |
| II-3 | 3-pyridyl | 4-(trifluoromethyl)pyridin-2-yl | CH₃ | | |
| II-4 | 1,5-dimethyl-1H-pyrazol-4-yl | 3-tert-butyl-1H-pyrazol-5-yl | CH₃ | | |
| II-5 | 1,5-dimethyl-1H-pyrazol-4-yl | 3-tert-butyl-1-methyl-1H-pyrazol-5-yl | CH₃ | | |
| II-6 | 1,5-dimethyl-1H-pyrazol-4-yl | 3-tert-butyl-1-(4-chlorophenyl)-1H-pyrazol-5-yl | CH₃ | | |

-continued

| Example | R¹ | R² | R³ | $t_{Ret}$(HPLC) [min] | MS (M + H)⁺ |
|---|---|---|---|---|---|
| II-7 | (1-methyl-5-methylpyrazol-4-yl) | 4-CF₃-pyridin-2-yl | CH₃ | | |
| II-8 | (1-methyl-5-methylpyrazol-4-yl) | 5-tert-butyl-isoxazol-3-yl | CH₃ | | |
| II-9 | (1-methyl-5-methylpyrazol-4-yl) | 3-tert-butyl-isoxazol-5-yl | CH₃ | | |
| II-10 | (1-methyl-5-methylpyrazol-4-yl) | 3-CF₃-1-methylpyrazol-5-yl (with extra F) | CH₃ | | |

Synthesis of Examples III-1 to III-10

Method of Synthesising E-1a:

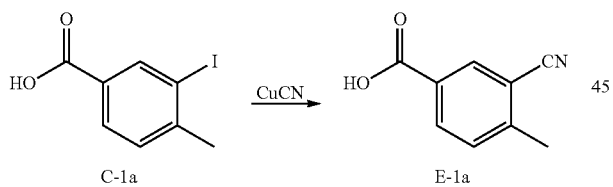

C-1a (1.00 g, 3.82 mmol) is placed in anhydrous DMF (4 mL), combined with CuCN (449 mg, 4.96 mmol) and stirred at 100° C. for 20 h. Aqueous working up and evaporation using the rotary evaporator yields E-1a (HPLC-MS: $t_{Ret}$=1.39 min; MS (M+H)⁺=162). Analogously to this method further compounds E-1 are obtained from the corresponding 3-iodo-benzoic acids.

General Method of Synthesising Intermediates E-2

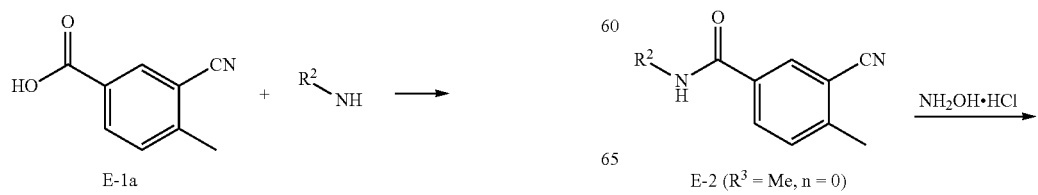

E-1a (1.00 mmol) in anhydrous THF/DCM (8 mL, 1:1) is combined dropwise with oxalyl chloride (1.10 mmol) and one drop of DMF. The mixture is stirred for 2 h at RT and the mixture is then evaporated down completely using the rotary evaporator. The residue is taken up in DCM and combined with THF (1 mL). A solution of the amine (1.10 mmol) in THF and Hünig-base (3.00 mmol) are added dropwise and the mixture is stirred for 3 h at RT. Aqueous working up and recrystallisation from EtOH yields the compounds E-2. Analogously to this method compounds E-2 are generally obtained from the corresponding E-1 intermediates.

General Method of Synthesising Intermediates E-3

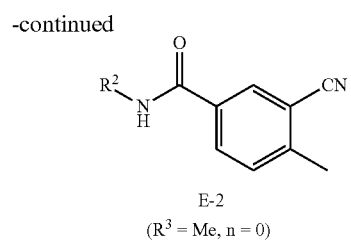

-continued

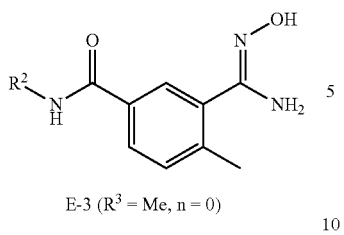

E-3 (R³ = Me, n = 0)

E-2 (1.00 mmol), hydroxylamine hydrochloride (2.20 mmol) and NEt₃ (2.50 mmol) are refluxed in EtOH (2.5 mL) for 2 h. Evaporation using the rotary evaporator and chromatographic purification by RP-HPLC yields the compounds E-3.

Analogously to this method compounds E-3 generally are obtained from the corresponding E-2 intermediates.

General Method of Synthesising Compounds of Type III

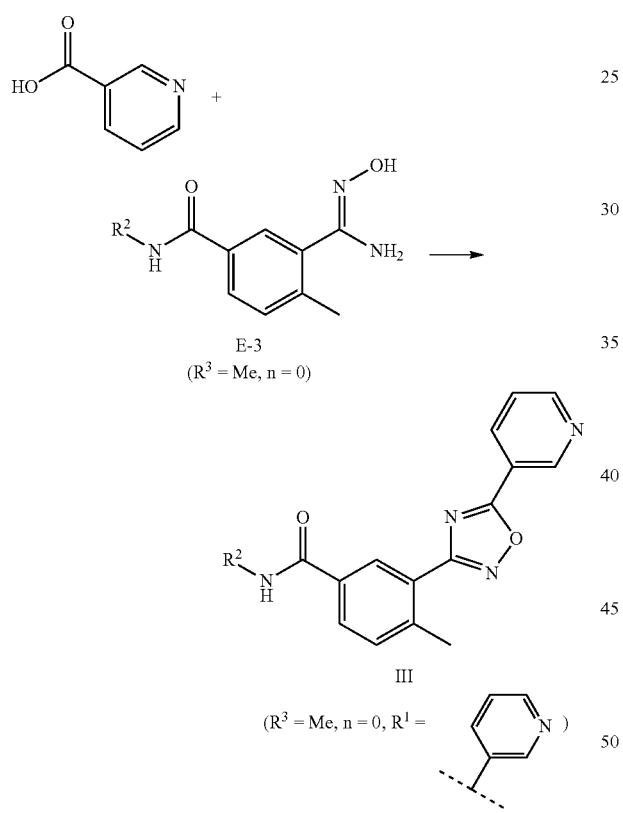

The carboxylic acid (1.00 mmol) is dissolved in DMF (4.5 mL), combined with Hünig base (4.00 mmol) and TBTU (1.00 mmol) and stirred at RT for 15 min. Then E-3 (0.90 mmol) is added and the mixture is stirred for 3 h at RT. The mixture is briefly heated to 100° C. After cooling and chromatographic purification by RP-HPLC compounds of type II are obtained.

Analogously to this method additional compounds of type III are obtained from the corresponding intermediates E-3 and the corresponding carboxylic acids (cf the Table that follows).

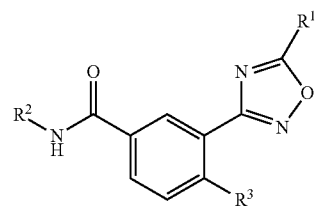

Examples III-1 to III-10

| # | R¹ | R² | R³ | $t_{Ret}$ (HPLC) [min] | MS (M + H)⁺ |
|---|---|---|---|---|---|
| III-1 | 3-pyridyl | 4-CF₃-pyridin-2-yl | CH₃ | | |
| III-2 | 3-pyridyl | 3-tBu-1-Me-pyrazol-5-yl | CH₃ | | |
| III-3 | 3-pyridyl | 3-tBu-isoxazol-5-yl | CH₃ | | |
| III-4 | 3-pyridyl | 3-tBu-1H-pyrazol-5-yl | CH₃ | | |
| III-5 | 3-pyridyl | 4-tBu-thiazol-2-yl | CH₃ | | |
| III-6 | 1,5-diMe-pyrazol-4-yl | 4-CF₃-pyridin-2-yl | CH₃ | | |
| III-7 | 1,5-diMe-pyrazol-4-yl | 3-tBu-1-Me-pyrazol-5-yl | CH₃ | | |

| # | R¹ | R² | R³ | $t_{Ret}$ (HPLC) [min] | MS (M+H)⁺ |
|---|---|---|---|---|---|
| III-8 | 1,5-dimethylpyrazol-4-yl | tert-butyl-isoxazol-3-yl | CH₃ | | |
| III-9 | 1,5-dimethylpyrazol-4-yl | tert-butyl-pyrazol-5-yl | CH₃ | | |
| III-10 | 1,5-dimethylpyrazol-4-yl | tert-butyl-thiazol-2-yl | CH₃ | | |

Synthesis of Examples IV-1 to IV-10

General Method of Synthesising Intermediates E-4

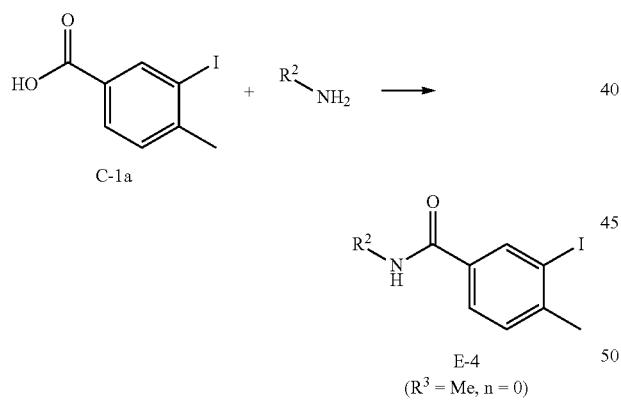

Benzoic acid C-1a (1.00 mmol) is dissolved in 10 mL anhydrous DCM/THF (2:1) and combined dropwise with oxalyl chloride (1.05 mmol). Then a few drops of DMF are added and the mixture is stirred for 2 h at RT. The mixture is evaporated down completely using the rotary evaporator, dissolved in 5 mL DCM and a solution of the amine (0.95 mmol) and Hünig base in THF (2.80 mmol) is added dropwise. Then the mixture is stirred for 3 h at RT. After aqueous working up and recrystallisation from EtOH the compounds E-4 are obtained.

Analogously to this method additional compounds E-4 are obtained from the corresponding 3-iodobenzoic acids and the corresponding amines R²—NH₂.

General Method of Synthesising Intermediates E-5

E-4 (1.00 mmol) is dissolved in anhydrous THF (20 mL) under protective gas, cooled to −20° C. and combined with iPrMgCl solution (2.20 mL, 1.8 M). The mixture is stirred for 2 h at this temperature. Then CO₂ is passed through the reaction mixture. After 1 h, NH₄Cl solution is added and the mixture is extracted twice with EE. The combined organic phases are extracted three times with 2M NaOH solution and the combined aqueous phases are then acidified with 6M HCl and extracted several times with EE. Drying on Na₂SO₄ and evaporation using the rotary evaporator yields compounds E-5.

Additional compounds E-5 are obtained from the corresponding compounds E-4 analogously to this method.

General Method of Synthesising Compounds of Type IV a) 3-cyanopyridine (1.00 mmol), hydroxylamine hydrochloride (2.20 mmol) and NEt₃ (2.20 mmol) are refluxed in MeOH (2.5 mL) for 2 h. Then the reaction mixture is evaporated down using the rotary evaporator and worked up under aqueous conditions. The hydroxylamidine E-6a is obtained (HPLC-MS: $t_{Ret}$=0.00 min; MS (M+H)$^+$=138).

Analogously to this method hydroxylamidines E-6 generally are obtained from the corresponding nitriles.

b) E-5 (1.00 mmol) is dissolved in DMF (5 mL), combined with Hünig base (5.00 mmol) and TBTU (1.00 mmol) and stirred for 15 min at RT. Then E-6a (1.15 mmol) is added and the mixture is stirred for 4 d at RT. After aqueous working up and evaporation using the rotary evaporator the residue is taken up in DMF (5 mL) and stirred for 4 h at 110° C. After cooling, compounds of type IV by way of example are obtained by chromatographic purification by RP-HPLC.

Analogously to the methods described hereinbefore the compounds of type IV in general are synthesised using the corresponding amine R$^2$—NH$_2$ and the corresponding nitrile R$^1$—CN (cf. the Table that follows).

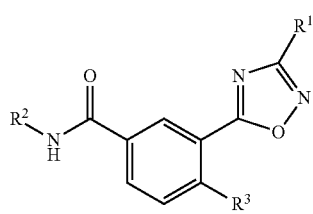

Example IV-1 to IV-10

| # | R$^1$ | R$^2$ | R$^3$ | $t_{Ret}$ (HPLC) [min] | MS (M+H)$^+$ |
|---|---|---|---|---|---|
| IV-1 | 3-pyridyl | 4-CF$_3$-pyridyl | CH$_3$ | | |
| IV-2 | 3-pyridyl | t-Bu-pyrazolyl | CH$_3$ | | |
| IV-3 | 3-pyridyl | t-Bu-isoxazolyl | CH$_3$ | | |
| IV-4 | 3-pyridyl | t-Bu-pyrazolyl (NH) | CH$_3$ | | |
| IV-5 | 3-pyridyl | t-Bu-thiazolyl | CH$_3$ | | |
| IV-6 | Me-pyrazolyl | 4-CF$_3$-pyridyl | CH$_3$ | | |
| IV-7 | Me-pyrazolyl | t-Bu-pyrazolyl | CH$_3$ | | |
| IV-8 | Me-pyrazolyl | t-Bu-isoxazolyl | CH$_3$ | | |
| IV-9 | Me-pyrazolyl | t-Bu-pyrazolyl (NH) | CH$_3$ | | |
| IV-10 | Me-pyrazolyl | t-Bu-thiazolyl | CH$_3$ | | |

Synthesis of Examples V-1, V-2, VI-1 and VI-2

Compounds of general type V and VI are obtained by generally known methods according to the synthesis routes shown in reaction scheme F.

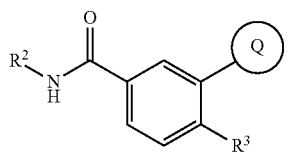

V-1/V-2 and VI-1/VI-2

| # | R¹ | R² | R³ | Q----(R¹) | $t_{Ret}$ (HPLC) [min] | MS $(M+H)^+$ |
|---|----|----|----|-----------|------------------------|--------------|
| V-1 | pyridin-3-yl | 5-tert-butyl-isoxazol-3-yl | CH₃ | 5-R¹-thiazol-2-yl | | |
| V-2 | pyridin-3-yl | 5-tert-butyl-isoxazol-3-yl | CH₃ | 4-R¹-thiazol-2-yl | | |
| VI-1 | pyridin-3-yl | 5-tert-butyl-isoxazol-3-yl | CH₃ | 2-R¹-thiazol-5-yl | | |
| VI-2 | pyridin-3-yl | 5-tert-butyl-isoxazol-3-yl | CH₃ | 2-R¹-thiazol-4-yl | | |

Synthesis of Compounds of Type VII

General Method of Synthesising the Intermediates G-1

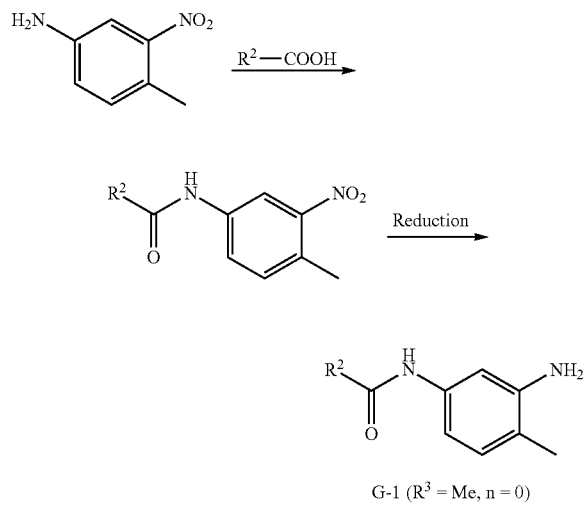

G-1 (R³ = Me, n = 0)

The carboxylic acid R²—COOH (1.00 mmol) is placed in DCM (5 mL), combined with SOCl₂ (3.00 mmol) and catalytic amounts of DMF and stirred for 15 h at 120° C. Then the mixture is azeotropically evaporated down with toluene several times using the rotary evaporator. The residue is taken up in 5 mL DCM, combined with nitroaniline (1.00 mmol) and Hünig base (1.00 mmol) and stirred for 2 h at RT. The reaction mixture is then diluted with DCM (10 mL) and extracted under aqueous conditions. By drying on MgSO₄ and evaporating the organic phase the amide is obtained, which is reacted further without any further purification steps.

The amide obtained (1.00 mmol) is taken up in MeOH (5 mL), combined with NH₄Cl soln. (0.5 mmol in 5 mL H₂O) and heated to 75° C. Then iron powder (5.00 mmol) is added batchwise and the mixture is stirred for 30 min at 75° C. After removal of the excess iron (using a magnet) and evaporation of the reaction mixture using the rotary evaporator, the compounds G-1 are precipitated out of the remaining aqueous phase. (N.B.: If the compound does not precipitate, G-1 may also be obtained by extraction or by chromatographic methods. Moreover, the nitro group may also be reduced using other methods known from the literature, such as for example catalytic hydrogenation with catalytic amounts of Pd/C or reduction using methods known from the literature with SnCl₂ in hydrochloric acid.) Analogously to this method 3-nitroanilines in general are reacted to form compounds G-1.

General Method of Synthesising the Intermediates G-2

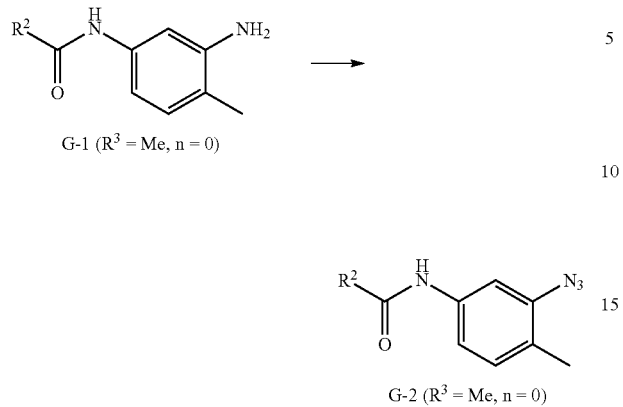

Anilines G-1 (1.00 mmol) are dissolved in 10 mL 2M HCl and 10 mL THF and cooled to 0° C. At this temperature NaNO₂ soln. (1.20 mmol in 5 mL H₂O) is added and the mixture is stirred for 60 min. Then NaN₃ soln. (1.10 mmol in 5 mL H₂O) is slowly added at 0° C. The reaction mixture is stirred for 30 min at 0° C. and then for 1 h at RT. After aqueous working up the compounds G-2 are obtained, which are further reacted without any further purification steps.

Analogously to this method the compounds G-2 in general are obtained from the compounds G-1.

General Method of Synthesising Compounds of Type VII

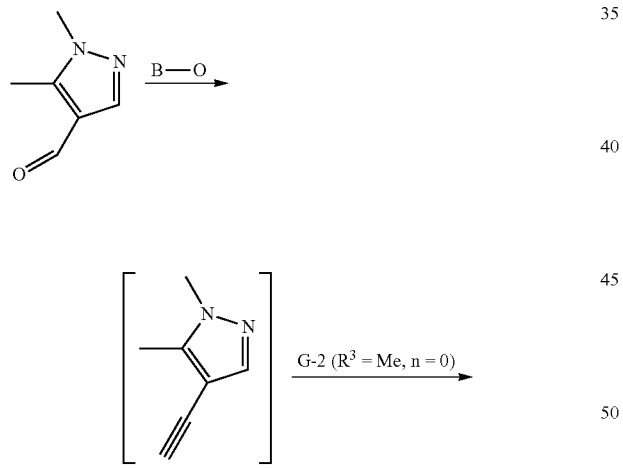

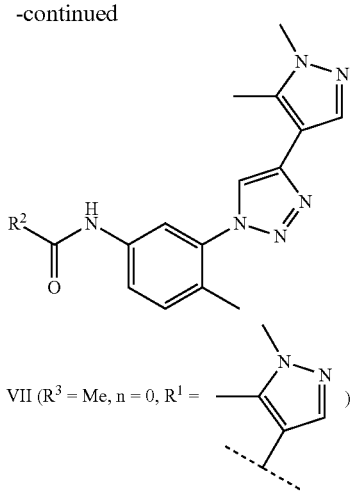

1,5-dimethylpyrazole-4-carbaldehyde (1.50 mmol) and Bestmann-Ohira reagent (B-O, 2.40 mmol) are placed in methanol (7.5 mL) and combined with potassium carbonate (3.40 mmol). After 12 h stirring at RT the corresponding azide G-2 (1.00 mmol) is added and the mixture is stirred. 1.1 mL of a 1M sodium ascorbate soln. (1.10 mmol) and 2.0 mL of a 0.1M CuSO₄ soln. (0.20 mmol) are added and the mixture is stirred for 7 d at 40° C.

For working up the mixture is evaporated down under reduced pressure, mixed with water and by the addition of 2M HCl soln. an acid pH is obtained. The mixture is then repeatedly extracted with EE, the combined organic phases are dried on MgSO₄, filtered and evaporated down under reduced pressure. By chromatographic purification by RP-HPLC the compounds VII-1 to VII-5 are obtained. The compounds VII-6, VII-7 and VII-8 are obtained by an analogous method from the corresponding commercially obtainable 3-pyridylethyne.

Analogously to the methods described hereinbefore the compounds of type VII are generally synthesised using the corresponding aldehyde R¹—CHO and the corresponding azide G-2.

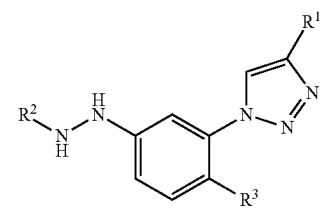

Examples VII-1 to VII-15

| Example | R¹ | R² | R³ | $t_{Ret}$ (HPLC) [min] | MS (M + H)⁺ |
|---|---|---|---|---|---|
| VII-1 | (1,5-dimethylpyrazol-4-yl) | CF₃ | CH₃ | | |

-continued

| Example | R¹ | R² | R³ | t_Ret (HPLC) [min] | MS (M + H)⁺ |
|---------|----|----|----|---------------------|-------------|
| VII-2 | 1,5-dimethyl-pyrazol-4-yl | 3-tert-butyl-1-methyl-pyrazol-5-yl | CH₃ | | |
| VII-3 | 1,5-dimethyl-pyrazol-4-yl | 5-tert-butyl-isoxazol-3-yl | CH₃ | | |
| VII-4 | 1,5-dimethyl-pyrazol-4-yl | 3-tert-butyl-1H-pyrazol-5-yl | CH₃ | | |
| VII-5 | 1,5-dimethyl-pyrazol-4-yl | 4-tert-butyl-thiazol-2-yl | CH₃ | | |
| VII-6 | pyridin-3-yl | 4-trifluoromethyl-pyridin-2-yl | CH₃ | | |
| VII-7 | 5-methoxy-pyridin-3-yl | 3-tert-butyl-1-methyl-pyrazol-5-yl | CH₃ | | |
| VII-8 | pyridazin-4-yl | 5-tert-butyl-isoxazol-3-yl | CH₃ | | |

| Example | R¹ | R² | R³ | $t_{Ret}$ (HPLC) [min] | MS (M + H)⁺ |
|---|---|---|---|---|---|
| VII-9 | 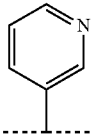 | 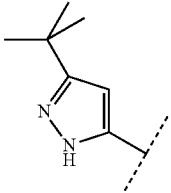 | CH₃ | | |
| VII-10 | 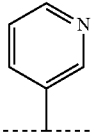 | 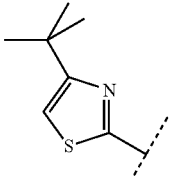 | CH₃ | | |
| VII-11 | 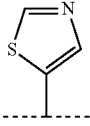 | 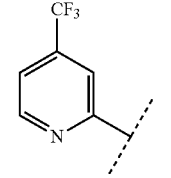 | CH₃ | | |
| VII-12 | 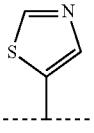 | 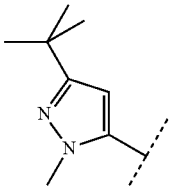 | CH₃ | | |
| VII-13 | 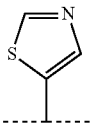 | 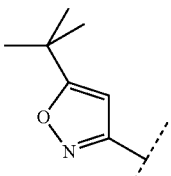 | CH₃ | | |
| VII-14 | 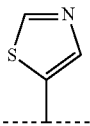 | 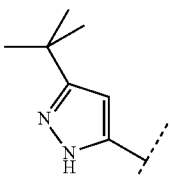 | CH₃ | | |
| VII-15 | 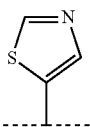 | 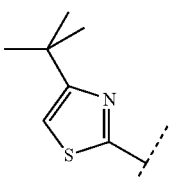 | CH₃ | | |

Synthesis of Compounds of Type VIII

Compounds of general type VIII are obtained by generally known methods according to the synthesis routes shown in reaction scheme H.

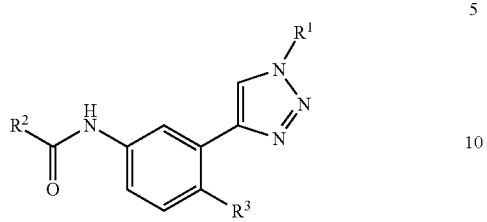

Examples VIII-1 to VIII-10

| # | R$^1$ | R$^2$ | R$^3$ | t$_{Ret}$ (HPLC) [min] | MS (M + H)$^+$ |
|---|---|---|---|---|---|
| VIII-1 | 1,5-dimethylpyrazol-4-yl | 4-CF$_3$-pyridin-2-yl (via C(CH$_3$)$_2$) | CH$_3$ | | |
| VIII-2 | 1,5-dimethylpyrazol-4-yl | 1-methylpyrazol-3,5-diyl (via C(CH$_3$)$_2$) | CH$_3$ | | |
| VIII-3 | 1,5-dimethylpyrazol-4-yl | isoxazol-3,5-diyl (via C(CH$_3$)$_2$) | CH$_3$ | | |
| VIII-4 | 1,5-dimethylpyrazol-4-yl | 1H-pyrazol-3,5-diyl (via C(CH$_3$)$_2$) | CH$_3$ | | |
| VIII-5 | 1,5-dimethylpyrazol-4-yl | thiazol-2,4-diyl | CH$_3$ | | |

-continued

| # | R¹ | R² | R³ | $t_{Ret}$ (HPLC) [min] | MS (M + H)⁺ |
|---|---|---|---|---|---|
| VIII-6 | 3-pyridyl | 4-CF₃-pyridin-2-yl | CH₃ | | |
| VIII-7 | 3-pyridyl | 3-tert-butyl-1-methyl-pyrazol-5-yl | CH₃ | | |
| VIII-8 | 3-pyridyl | 3-tert-butyl-isoxazol-5-yl | CH₃ | | |
| VIII-9 | 3-pyridyl | 3-tert-butyl-1H-pyrazol-5-yl | CH₃ | | |
| VIII-10 | 3-pyridyl | 4-tert-butyl-thiazol-2-yl | CH₃ | | |

The following Examples describe the biological activity of the compounds according to the invention without restricting the invention to these Examples.

Compounds of general formula (1) are characterised by their wide range of applications in the therapeutic field. Particular mention should be made of those applications in which the inhibition of specific signal enzymes, particularly the inhibiting effect on the proliferation of cultivated human tumour cells but also the proliferation of other cells, such as endothelial cells, for example, plays a part.

Kinase Test B-Raf (V600E)

In a dilution series, 10 μL aliquots of test substance solution are placed in a multiwell plate. The dilution series is selected so as to cover a range of concentrations from 50 μM to 1 nM. The final concentration of DMSO is 5%.

10 μL of the B-Raf (V600E) kinase solution are pipetted in (containing 2.5 ng B-Raf (V600E)-kinase in 20 mM TrisHCl pH 7.5, 0.1 mM EDTA, 0.1 mM EGTA, 0.286 mM sodium orthovanadate, 10% glycerol, 1 mg/mL bovine serum albumin, 1 mM dithiothreitol) and incubated for 24 h at RT with agitation. The kinase reaction is started by the addition of 20 μL ATP solution [625 μM ATP, 75 mM TrisHCl pH 7.5, 0.05% Brij, 0.5 mM sodium orthovanadate, 25 mM magnesium acetate, phosphatise cocktail (Sigma P2850, dilution recommended by the manufacturer), 0.25 mM EGTA] and 10 μL MEK1 solution [containing 50 ng biotinylated MEK1 (prepared from purified MEK1 according to standard procedure, e.g. with reagent EZ-Link Sulfo-NHS-LC-Biotin, Pierce 21335) in 20 mM TrisHCl pH 7.5, 0.1 mM EDTA, 0.1 mM EGTA, 0.286 mM sodium orthovanadate, 10% glycerol, 1 mg/mL bovine serum albumin, 1 mM dithiothreitol] and carried out for 60 min at RT with constant agitation. The reaction is stopped by the addition of 12 μL of a 100 mM EDTA solution and incubated for a further 5 min.

55 μL of the reaction solution are transferred into a streptavidine-coated plate (e.g. Streptawell HighBond, Roche #11989685) and shaken gently for 1 h at RT, in order to bind biotinylated MEK1 to the plate. After removal of the liquid the plate is washed three times with 200 μL of 1×PBS, and 100 μL solution of primary antibody plus europium-labelled secondary antibody [Anti Phospho-MEK (Ser217/221), Cell Signaling #9121 and Eu-N1 labeled anti-rabbit antibody, Perkin Elmer #AD01015], each diluted 1:2000 in Delfia Assay Buffer (Perkin Elmer 4002-0010), is added. After 1 h agitation at RT the solution is poured away and washed three times with 200 µL Delfia Wash Buffer (Perkin Elmer #4010-0010). After the addition of 200 µL Enhancement Solution (Perkin Elmer 4001-0010) the preparation is shaken for 10 min at RT and then measured in a Wallac Victor using the programme "Delfia Time Resolved Fluorescence (Europium)".

$IC_{50}$ values are determined from these dosage-activity curves using Standard Levenburg Marquard algorithms (GraphPadPrizm).

Most compounds of type I-VIII exhibit a good to very good inhibitory effect in this B-Raf (V600E) inhibition test, i.e. they have an $IC_{50}$ value of less than 1 µM, generally less than 100 nM.

Measurement of the Inhibition of Proliferation on Cultivated Human Melanoma Cells (SK-MEL28)

To measure proliferation on cultivated human tumour cells, cells of melanoma cell line SK-MEL28 [American Type Culture Collection (ATCC)] are cultivated in MEM medium, supplemented with 10% foetal calf serum, 0.15% $NaHCO_3$, 1 mM sodium pyruvate, 1% non-essential amino acids (Gibco 11140-035) and 2 mM glutamine SK-MEL28 cells are in 96-well flat-bottomed plates at a density of 2500 cells per well in supplemented MEM medium (see above) and incubated overnight in an incubator (at 37° C. and 5% $CO_2$). The active substances are added to the cells in various concentrations so as to cover a range of concentrations from 50 µM to 1 nM. After a further 72 hours incubation, 20 µl Alamar-Blue reagent (Serotec Ltd.) is added to each well, and the cells are incubated for a further 3-6 hours. The colour change of the AlamarBlue reagent is determined in a fluorescence spectrophotometer (e.g. Gemini, Molecular Devices). $EC_{50}$ values are calculated using Standard Levenburg Marquard algorithms (GraphPadPrizm).

Measurement of the Inhibition of the Raf Signal Transduction Cascade (Phosphorylation Status of ERK)

Activating B-Raf triggers a signal transduction cascade, which leads to the phosphorylation and activation of MEK and, as a consequence, to the specific phosphorylation of ERK. The measurement of the phosphorylation status on the ERK protein is used as a measurement of the cellular activity of Raf proteins.

The human melanoma cell line SK-MEL28 is cultivated in MEM medium, supplemented with 10% foetal calf serum, 0.15% $NaHCO_3$, 1 mM sodium pyruvate, 1% non-essential amino acids (Gibco 11140-035) and 2 mM glutamine 7500 cells are seeded in a multiwell plate and incubated overnight in an incubator (at 37° C. and 5% $CO_2$). The active substances are added to the cells in different concentrations, so as to cover a range of concentractions from 50 µM to 1 nM. After the substances have been left to work for 2 h the supernatant is removed and the cells are treated with 150 µL of 4% formaldehyde solution (in 1×PBS) for 20 min After the removal of the formaldehyde solution the cells are permeabilised five times, each time with 200 µL of 0.1% Triton X100 (in 1×PBS) for 5 min and then treated with 150 µL of blocking solution [5% powdered milk in TB ST (10 mM Tris HCl pH 8.0, 150 mM NaCl, 0.05% Tween)] for a period of 90 min. The blocking solution is removed, replaced by 50 µL of a solution with primary antibody (mouse anti-pERK1&2, Sigma M8159, diluted 1:500 in blocking solution, see above) and incubated overnight at 4° C. After elimination of the solution and washing five times with 0.1% Tween (in 1×PBS) for 5 min in each case the cells are incubated for 1 h with 50 µL of a solution of the secondary antibody (rabbit-antimouse, coupled to horseradish peroxidase, e.g. DAKO PO161, diluted 1:1000 in blocking solution, see above). The solution containing secondary antibody is removed, washed five times with 0.1% Tween (in 1×PBS) for 5 min in each case and a peroxidise reaction is carried out. For this, 100 µL of the staining solution, a 1:1 mixture of TMB peroxidase substrate (e.g. Kirkegaard & Perry Laboratories #50-76-02) and peroxidase solution B ($H_2O_2$, e.g. Kirkegaard & Perry Laboratories #50-65-02) is added and the mixture is incubated for 5-20 min. The reaction is ended by the addition of 100 µL 1 M phosphoric acid and the absorption is determined at a wavelength of 450 nm in a photometer (e.g. SpectraMax Plus, Molecular Devices). Standard Levenburg Marquard algorithms (GraphPadPrizm) are used to calculate the $EC_{50}$ values from the dosage-activity curves.

Most compounds of type I-VIII exhibit a good to very good activity in the two cellular assays described, i.e. they have an $EC_{50}$ value of less than 5 µM.

The substances of the present invention are B-Raf kinase inhibitors. As can be demonstrated by DNA staining followed by FACS or Cellomics Array Scan analysis, the inhibition of proliferation achieved by the compounds according to the invention is brought about primarily by preventing entry into the DNA synthesis phase. The treated cells arrest in the G1 phase of the cell cycle. Because of their biological properties the compounds of general formula (1) according to the invention, the isomers, pharmacologically acceptable salts and polymorphs thereof are therefore suitable for the treatment of diseases characterised by excessive or abnormal cell proliferation.

Accordingly, the compounds according to the invention are also tested on other tumour cells. For example these compounds are active on the colon carcinoma cell line Colo205 and can be used for this indication. This demonstrates the usefulness of the compounds according to the invention for treating various type of tumours.

Examples of diseases with excessive or abnormal cell proliferation include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also useful for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples that follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:
1. A compound of formula (1)

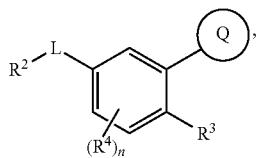

wherein
Q has a partial structure

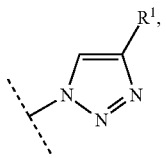

L is selected from among —NHC(O)—, —NHC(S)—, —C(O)—, —C(S)—, —NH—, —S(O)—, —S(O)O—, —S(O)$_2$—, —S(O)$_2$O—, —S(O)NH—, —S(O)$_2$NH—, —OS(O)—, —OS(O)$_2$—, —OS(O)NH—, —OS(O)$_2$NH—, —C(O)O—, —C(O)S—, —C(NH)NH—, —OC(O)—, —OC(O)O—, —OC(O)NH—, —SC(O)—, —SC(O)O—, —SC(O)NH—, —NHC(NH)—, —NHS(O)—, —NHS(O)O—, —NHS(O)$_2$—, —NHS(O)$_2$O—, —NHS(O)$_2$NH—, —NHC(O)O—, —NHC(O)NH— and —NHC(S)NH— or denotes a bond, $R^1$ is selected from among $R^a$ and $R^b$, $R^2$ is furyl, thienyl, pyrrolyl, oxazolyl, thiazolyl, isoxazolyl, isothiazolyl, imidazolyl, triazolyl, tetrazolyl, oxadiazolyl, thiadiazolyl, pyrimidyl, pyridazinyl, pyrazinyl, or triazinyl, said $R^2$ being optionally substituted by one or more, identical or different $R^{5b}$, $R^3$ and each $R^4$ is in each case independently selected from among hydrogen, halogen, —CN, —NO$_2$, —NR$^h$R$^h$, —OR$^h$, —C(O)R$^h$, —C(O)NR$^h$R$^h$, —SR$^h$, —S(O)R$^h$, —S(O)$_2$R$^h$, C$_{1-4}$alkyl, C$_{1-4}$haloalkyl, C$_{3-7}$cycloalkyl and 3-7 membered heterocycloalkyl, $R^{5b}$ is selected from among $R^a$ and $R^b$, n has the value 0, 1, 2 or 3, each $R^a$ independently of one another denotes hydrogen or a group optionally substituted by one or more identical or different $R^b$ and/or $R^c$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is in each case independently selected from among =O, —OR$^c$, C$_{1-3}$haloalkyloxy, —OCF$_3$, =S, —SR$^c$, =NR$^c$, =NOR$^c$, =NNR$^c$R$^c$, =NN(NR$_g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N {[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$ and —N(R$^g$)C(NR$^g$)NR$^c$R$^c$, each $R^c$ in each case independently of one another denotes hydrogen or a group optionally substituted by one or more identical or different $R^d$ and/or $R^e$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, each $R^d$ denotes a suitable group and is in each case independently selected from among =O, —OR$^e$, C$_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R.sup.g)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R.g)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$, each $R^e$ in each case independently of one another denotes hydrogen or a group optionally substituted by one or more identical or different $R^f$ and/or $R^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, each $R^f$ denotes a suitable group and is in each case independently selected from among =O, —OR$^g$, C$_{1-3}$haloalkyloxy, —OCF$_3$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)

$R^g$, —S(O)O$R^g$, —S(O)$_2$$R^g$, —S(O)$_2$O$R^g$, —S(O)N$R^g$$R^g$, —S(O)$_2$N$R^g$$R^g$, —OS(O)$R^g$, —OS(O)$_2$$R^g$, —OS(O)$_2$O$R^g$, —OS(O)N$R^g$$R^g$, —OS(O)$_2$N$R^g$$R^g$, —C(O)$R^g$, —C(O)O$R^g$, —C(O)S$R^g$, —C(O)N$R^g$$R^g$, —C(O)N($R^h$)N$R^g$$R^g$, —C(O)N($R^h$)O$R^g$, —C(N$R^h$)N$R^g$$R^g$, —C(NOH)$R^g$, —C(NOH)N$R^g$$R^g$, —OC(O)$R^g$, —OC(O)O$R^g$, —OC(O)S$R^g$, —OC(O)N$R^g$$R^g$, —OC(N$R^h$)N$R^g$$R^g$, —SC(O)$R^g$, —SC(O)O$R^g$, —SC(O)N$R^g$$R^g$, —SC(N$R^h$)N$R^g$$R^g$, —N($R^h$)C(O)$R^g$, —N[C(O)$R^g$]$_2$, —N(O$R^h$)C(O)$R^g$, —N($R^h$)C(N$R^h$)$R^g$, —N($R^h$)N($R^h$)C(O)$R^g$, —N[C(O)$R^g$]N$R^g$$R^g$, —N($R^h$)C(S)$R^g$, —N($R^h$)S(O)$R^g$, —N($R^h$)S(O)O$R^g$, —N($R^h$)S(O)$_2$$R^g$, —N[S(O)$_2$$R^g$]$_2$, —N($R^h$)S(O)$_2$O$R^g$, —N($R^h$)S(O)$_2$N$R^g$$R^g$, —N($R^h$)[S(O)$_2$]$_2$$R^g$, —N($R^h$)C(O)O$R^g$, —N($R^h$)C(O)S$R^g$, —N($R^h$)C(O)N$R^g$$R^g$, —N($R^h$)C(O)N$R^h$N$R^g$$R^g$, —N($R^h$)N($R^h$)C(O)N$R^g$$R^g$, —N($R^h$)C(S)N$R^g$$R^g$, —[N($R^h$)C(O)]$_2$$R^g$, —N($R^h$)[C(O)]$_2$$R^g$, —N{[C(O)]$_2$$R^g$}$_2$, —N($R^h$)[C(O)]$_2$O$R^g$, —N($R^h$)[C(O)]$_2$N$R^g$$R^g$, —N{[C(O)]$_2$O$R^g$}$_2$, —N{[C(O)]$_2$N$R^g$$R^g$}$_2$, —[N($R^h$)C(O)]$_2$O$R^g$, —N(O)C(N$R^h$)O$R^g$, —N($R^h$)C(NOH)$R^g$, —N($R^h$)C(N$R^h$)S$R^g$ and —N($R^h$)C(N$R^h$)N$R^g$$R^g$, each $R^g$ in each case independently of one another denotes hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^h$ is in each case independently selected from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of tautomers, racemates, enantiomers, diastereomers and the mixtures thereof with the proviso that formula (1) is not 5-(3-(4-benzyl-1H-1,2,3-triazol-1-yl)-4-chlorophenyl-6-ethylpyrimidine-2,4-diamine and 5-(4-chloro-3-(4-phenyl-1H-1,2,3-triazol-1-yl)phenyl)6-ethylpyrimidine-2,4-diamine.

2. The compound according to claim 1 wherein
L is selected from among —NHC(O)—, —S(O)NH—, —S(O)$_2$NH—, —C(NH)NH—, —NHC(NH)—, —NHS(O)— and —NHS(O)$_2$— or denotes a bond.

3. The compound according to claim 1 wherein
n has the value 0.

4. The compound according to claim 1 wherein
$R^1$ denotes a group optionally substituted by one or more identical or different $R^{b1}$ and/or $R^{c1}$, selected from among $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, or
$R^1$ is selected from among —C(O)O$R^{c1}$, —C(O)N$R^{c1}$$R^{c1}$ and —C(O)$R^{c1}$, each $R^{b1}$ denotes a suitable group and is in each case independently selected from among =O, —O$R^{c1}$, —S$R^{c1}$, —N$R^{c1}$$R^{c1}$, halogen, —CN, —NO$_2$, —C(O)$R^{c1}$, —C(O)O$R^{c1}$, —C(O)N$R^{c1}$$R^{c1}$, —NHC(O)$R^{c1}$, —NHC(O)O$R^{c1}$, —NHC(O)N$R^{c1}$$R^{c1}$, —S(O)$R^{c1}$ and —S(O)$_2$$R^{c1}$,
each $R^{c1}$ in each case independently of one another denotes hydrogen or a group optionally substituted by one or more identical or different $R^{d1}$ and/or $R^{e1}$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^{d1}$ a suitable group and is in each case independently selected from among =O, —O$R^{e1}$, —N$R^{e1}$$R^{e1}$, halogen, —CN, —NO$_2$, —C(O)$R^{e1}$, —C(O)O$R^{e1}$, —C(O)N$R^{e1}$$R^{e1}$, —OC(O)$R^{e1}$, —OC(O)O$R^{e1}$, —OC(O)N$R^{e1}$$R^{e1}$, —NHC(O)$R^{e1}$, —NHC(O)O$R^{e1}$ and —NHC(O)N$R^{e1}$$R^{e1}$ and each $R^{e1}$ is in each case independently selected from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl.

5. The compound according to claim 4, wherein
$R^1$ is a group optionally substituted by one or more identical or different $R^{b1}$ and/or $R^{c1}$, selected from among $C_{6-10}$aryl, $C_{7-16}$arylalkyl, 5-12 membered heteroaryl and 6-18 membered heteroarylalkyl.

6. The compound according to claim 5, wherein
$R^1$ is a group optionally substituted by one or more identical or different $R^{b1}$ and/or $R^{c1}$, selected from among pyridyl, pyrimidyl, thiazolyl, imidazolyl, triazolyl, pyrazolyl, pyrrolyl, furanyl, phenyl, benzyl, imidazo[2.1-b]thiazolyl, imidazo[1,2-a]pyridyl, thiazolyl-methyl and oxazolylmethyl.

7. The compound according to claim 1 wherein
each $R^{5b}$ independently of one another is selected from among $R^{a2}$ and $R^{b2}$,
each $R^{a2}$ is a group optionally substituted by one or more identical or different $R^{b2}$ and/or
$R^{c2}$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^{b2}$ denotes a suitable group and is in each case independently selected from among =O, —O$R^{c2}$, —S$R^{c2}$, —N$R^{c2}$$R^{c2}$, halogen, —CF$_3$, —CN, —NO$_2$, —S(O)$R^{c2}$, —S(O)$_2$$R^{c2}$, —S(O)N$R^{c2}$$R^{c2}$, —S(O)$_2$N$R^{c2}$$R^{c2}$, —C(O)$R^{c2}$, —C(O)O$R^{c2}$, —C(O)N$R^{c2}$$R^{c2}$, —OC(O)$R^{c2}$, —OC(O)O$R^{c2}$, —OC(O)N$R^{c2}$$R^{c2}$, —NHC(O)$R^{c2}$, —NHS(O)$_2$$R^{c2}$, —NHC(O)O$R^{c2}$, —NHC(O)N$R^{c2}$$R^{c2}$,
each $R^{c2}$ independently of one another denotes hydrogen or a group optionally substituted by one or more identical or different $R^{d2}$ and/or $R^{e2}$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^{d2}$ denotes a suitable group and is in each case independently selected from among =O, —O$R^{e2}$, —N$R^{e2}$$R^{e2}$, halogen, —CN, —NO$_2$, —C(O)$R^{e2}$, —C(O)O$R^{e2}$, —C(O)N$R^{e2}$$R^{e2}$, —OC(O)$R^{e2}$, —OC(O)O$R^{e2}$, —OC(O)N$R^{e2}$$R^{e2}$, —NHC(O)$R^{e2}$, —NHC(O)O$R^{e2}$ and —NHC(O)N$R^{e2}$$R^{e2}$ and
each $R^{e2}$ is in each case independently selected from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl.

8. A pharmaceutical composition comprising a compound or the pharmacologically acceptable salts thereof of formula (1) according to claim 1 together with a pharmacologically acceptable carrier or excipient.

9. A pharmaceutical composition comprising a compound or the pharmacologically acceptable salt thereof of formula (1) according to claim 1 together with at least one other cytostastic or cytotoxic active substance, different from the compound of formula (1), optionally in the form of the tautomers, the racemates, the enantiomers, the diastereomers and the mixtures thereof, and optionally the pharmacologically acceptable salts thereof.

10. The compound according to claim 1 wherein $R^2$ is isoxazolyl, thiazolyl, imidazolyl or oxazolyl, wherein $R^2$ is optionally substituted by one or more identical $R^{5b}$, which $R^{5b}$ may be the same or different.

11. The compound according to claim 2 wherein L is —NHC(O)—.

12. A method of inhibition of B-RAF kinase in a warm-blooded animal which comprises administering to the animal a therapeutically effective amount of a compound according to claim 1.

13. A method for the treatment of melanoma in a warm-blooded animal and which comprises administering to the animal a therapeutically effective amount of a compound according to claim 1.

* * * * *